(12) United States Patent
Wehlan et al.

(10) Patent No.: US 10,336,698 B2
(45) Date of Patent: Jul. 2, 2019

(54) PROCESS FOR THE PRODUCTION OF 2-[4-(CYCLOPROPANECARBONYL) PHENYL]-2-METHYL-PROPANENITRILE

(71) Applicant: SANOFI-AVENTIS DEUTSCHLAND GMBH, Frankfurt am Main (DE)

(72) Inventors: Hermut Wehlan, Frankfurt am Main (DE); Kai Rossen, Frankfurt am Main (DE); Alexander Schaefer, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 15/544,493

(22) PCT Filed: Jan. 21, 2016

(86) PCT No.: PCT/EP2016/051223
§ 371 (c)(1),
(2) Date: Jul. 18, 2017

(87) PCT Pub. No.: WO2016/116555
PCT Pub. Date: Jul. 28, 2016

(65) Prior Publication Data
US 2017/0369440 A1    Dec. 28, 2017

(30) Foreign Application Priority Data
Jan. 22, 2015 (EP) .................................. 15152101

(51) Int. Cl.
| | | |
|---|---|---|
| C07C 253/00 | (2006.01) | |
| C07C 253/32 | (2006.01) | |
| C07C 253/34 | (2006.01) | |
| C07D 211/22 | (2006.01) | |
| C07C 253/30 | (2006.01) | |

(52) U.S. Cl.
CPC .......... C07D 211/22 (2013.01); C07C 253/30 (2013.01); *C07C 2601/02* (2017.05)

(58) Field of Classification Search
CPC ... C07C 253/00; C07C 253/32; C07C 253/34; C07C 2601/02
See application file for complete search history.

(56) References Cited

U.S. PATENT DOCUMENTS

| | | | |
|---|---|---|---|
| 4,254,129 | A | 3/1981 | Carr et al. |
| 4,598,077 | A | 7/1986 | Fujii et al. |
| 5,059,615 | A | 10/1991 | Fugmann et al. |
| 5,420,322 | A | 5/1995 | Chiu et al. |
| 6,303,782 | B1 | 10/2001 | Caron |
| 6,340,761 | B1 | 1/2002 | Krauss et al. |
| 7,595,338 | B2 | 9/2009 | Wilk |
| 2003/0166682 | A1 | 9/2003 | Milla |
| 2005/0222154 | A1 | 10/2005 | Rehwinkel et al. |
| 2005/0288287 | A1 | 12/2005 | Fotouhi et al. |
| 2008/0221350 | A1 | 9/2008 | Meudt et al. |
| 2010/0249123 | A1 | 9/2010 | Bonnet et al. |
| 2012/0035122 | A1 | 2/2012 | Vaillancourt et al. |
| 2013/0045965 | A1 | 2/2013 | Brotherton-Pleiss et al. |
| 2015/0290192 | A1 | 10/2015 | Iyer et al. |

FOREIGN PATENT DOCUMENTS

WO    WO-2009/001127 A1    12/2008

OTHER PUBLICATIONS

Caubere, P. (1993). "Unimetal Super Bases," *Chem. Rev.* 93(6):2317-2334.
Chen, Y. et al. (1999; e-published on Aug. 18, 1999). "Synthesis and Properties of ABA Amphiphiles," *The Journal of Organic Chemistry* 64(18):6870-6873.
Di Giacomo, B. et al. (Sep. 30, 1999). "A New Synthesis of Carboxyterfenadine (Fexofenadine) and Its Bioisosteric Tetrazole Analogs," *Il Farmaco* 54(9):600-610.
Hanack, M. et al. (1963). "Note on Infrared Spectra of Cyclopropane Compounds," *Chem. Ber.* 96:2532-2536), with English Translation.
Huang, J. et al. (2010, e-published on Oct. 4, 2010). "Novel Preparation of $H_1$ Receptor Antagonist Fexofenadine," *Organic Process Research & Development* 14(6):1464-1468.
Idoux, J.P. et al. (Apr. 1994). "Densities, Viscosities, Speeds of Sound, and Water Solubilities of Some Polypropylene Glycol Ether Derivatives in the Temperature Range 273.15-323.15 K," *Journal of Chemical & Engineering Data* 39(2):261-265.
Kauffmann, T. et al. (Apr. 1992). "Aldehyde-Selective Cyanoalkylations With Cyanoalkyl Derivatives of Iron(II) and Other Transition Metals," *Chemische Berichte* 125(4):899-905, with English Translation.
Kauffmann, T. et al. (1992). "Anticheleselective Cyanoalkylations With Cyanoalkyl Derivatives of Iron(II), Titanium(IV) and Other Transition Metals," *Chemische Berichte* 125:907-912, with English Translation.
Makosza, M. et al. (1974). "Reactions of Organic Anions—L: Reactions of Phenylacetonitrile Derivatives with Aromatic Nitrocompounds in Basic Media," *Tetrahedron* 30(20): 3723-3735.
Mansell, S.M. et al. (Dec. 1-15, 2010; e-published on Aug. 20, 2010). "New $U^{III}$ and $U^{IV}$ Silylamides and an Improved Synthesis of $NaN(SiMe_2R)_2$ (R=Me, Ph)," *J. of Organometallic Chem.* 695(25-26):2814-2821.
Palmas, P. et al. (1994). "First Spectroscopic Evidence for Complex Bases: A $^{23}Na$ NMR Study of Solid $NaNH_2$-t-BuONa," *J. Am. Chem. Soc.* 116(25):11604-11605.
Rovnyak, G. et al. (May 1973). "Synthesis and Antiinflammatory Activities of (α-Cyclopropyl-p-Tolyl)Acetic Acid and Related Compounds," *Journal of Medicinal Chemistry* 16(5):487-490.
Schliemann, W. et al. (1980). "Synthese Einiger Von ω-Chlorbutyrophenonen Abgeleiteten Verbindungen," *Pharmazie* 35:140-143, with English Translation of the Abstract.
Schmitt, S. et al. (2013; e-published on Jan. 8, 2013). "Diastereoselective Syntheses of (3R,4R)- and (3R,4S)-4-Aryl-3-methyl-4-piperidinemethanol and Fluoro Analogues," *The Journal of Organic Chemistry* 78(3):1222-1229.

(Continued)

*Primary Examiner* — Noble E Jarrell
(74) *Attorney, Agent, or Firm* — Morrison & Foerster LLP

(57) ABSTRACT

A new process for the production of 2-[4-(cyclopropanecarbonyl)phenyl]-2-methyl-propanenitrile is described. This compound can be used for the production of drugs, such as Fexofenadine.

24 Claims, No Drawings

(56) References Cited

OTHER PUBLICATIONS

International Preliminary Report on Patentability dated Aug. 3, 2017 for PCT/EP2016/051223, Internationally filed on Jan. 21, 2016, eight pages.
International Search Report dated Mar. 23, 2016, for PCT/EP2016/051223, Internationally filed on Jan. 21, 2016, five pages.
Written Opinion of the International Searching Authority dated Mar. 23, 2016, for PCT/EP2016/051223, Internationally filed on Jan. 21, 2016, six pages.

PROCESS FOR THE PRODUCTION OF 2-[4-(CYCLOPROPANECARBONYL)PHENYL]-2-METHYL-PROPANENITRILE

CROSS REFERENCE TO RELATED APPLICATIONS

This application is a National Phase application under 35 U.S.C. § 371 of International Application No. PCT/EP2016/051223, filed on Jan. 21, 2016, which claims priority benefit of EP Application No. 15152101.0, filed on Jan. 22, 2015, the disclosures of each of which are herein incorporated by reference in their entirety.

BACKGROUND OF THE INVENTION

The present invention relates to a chemical process for the manufacture of 2-[4-(cyclopropanecarbonyl)phenyl]-2-methyl-propanenitrile, the compound of formula I, and its use as an intermediate in the production of drugs. For instance, 2-[4-(cyclopropanecarbonyl)phenyl]-2-methyl-propanenitrile is a key intermediate for the production of Fexofenadine, the compound of the formula II.

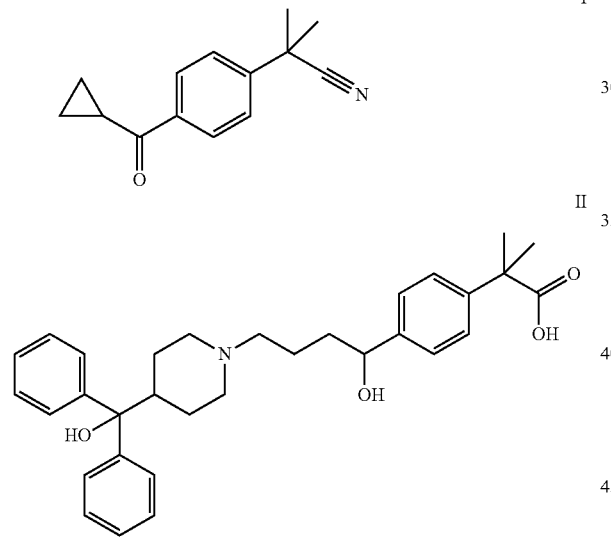

Fexofenadine II is an antihistamine pharmaceutical drug for the treatment of allergy symptoms and it is a broncho-dilator (U.S. Pat. No. 4,254,129, Richardson-Merrell Inc.).

2-[4-(cyclopropanecarbonyl)phenyl]-2-methyl-propanenitrile of the formula I is an intermediate in the synthesis of Fexofenadine and several prior art methods are described for its preparation. These methods involve procedures with a high number of intermediates as illustrated in scheme 1 below which summarizes such strategies. In U.S. Pat. No. 6,340,761, (Merrell Pharm. Inc.) the corresponding intermediates are prepared in examples 2, 3, 5 and 9 as follows. Starting from toluene III, the ketone of formula IV was obtained from Friedel-Crafts acylation with 4-chlorobutyryl chloride (Ex. 2), followed by cyclisation to yield the cyclopropyl compound V (Ex.3). The latter was brominated (compound VI) and the bromide was replaced by cyanide to yield 4-cyclopropanecarbonyl-phenyl)-acetonitrile VII (Ex. 5 and 7). Subsequent alkylation with methyl iodide furnished the desired intermediate of formula I (Ex. 9). These steps (from compounds of formula V to VII) are also described in the literature (J. Med. Chem 1973, 16, 487-490) wherein the compound of formula V was prepared starting from cyclopropylcarbonylchloride. The compound of formula I is thus obtained in a five step synthesis, involving several hazardous steps such as radical bromination, handling of highly toxic and industrially undesirable compounds such as cyanide and methyl iodide.

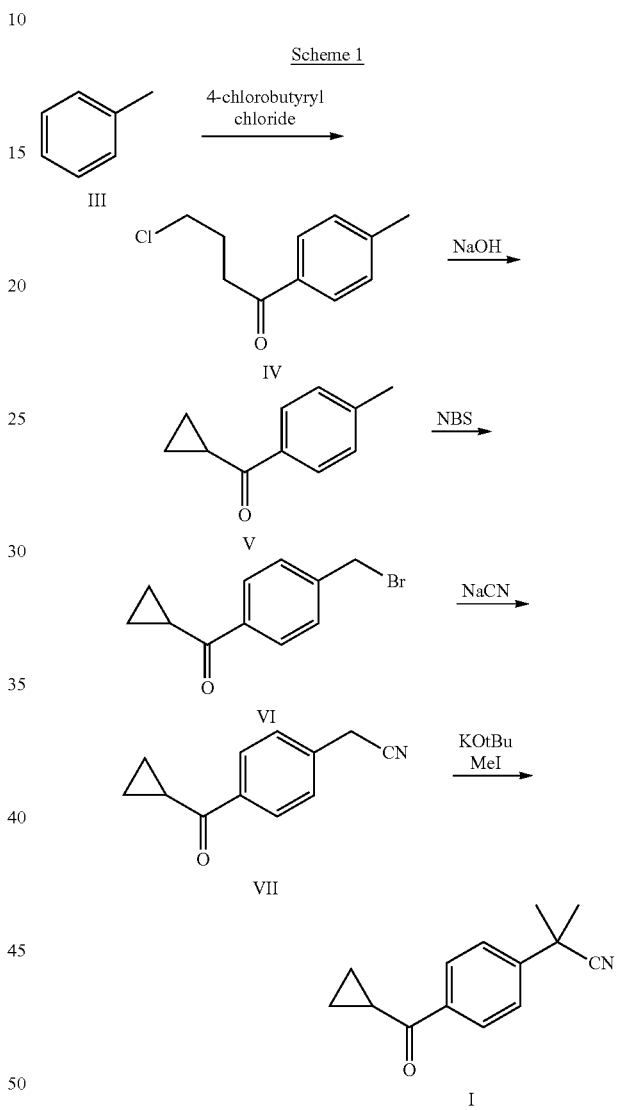

The preparation of the compound of formula I is further described by Wang et al. (Org. Proc. Res. and Dev. 2010, 14, 1464-68) according to scheme 2 below, wherein a compound of formula IX is converted into the compound of formula I in 4 synthetic steps consisting of alkylation of the compound of formula X via Claisen condensation to give the compound of formula XI, followed by thermal treatment to give a compound of formula XII (X=OH), functionalization to give a compound of formula XII (X=Br, Cl) and cyclisation. Even though compound of formula I is an unwanted by-product the specific conditions furnished the product up to 83% yield (Table 2, line 1). The starting material of formula IX can either be bought or and can be prepared from methyl p-toluate (VIII) in 2 steps (U.S. Pat. No. 4,598,077)

in analogy to the conversion of formula V to VII described in Scheme 1 above, resulting again in a costly multistep synthesis.

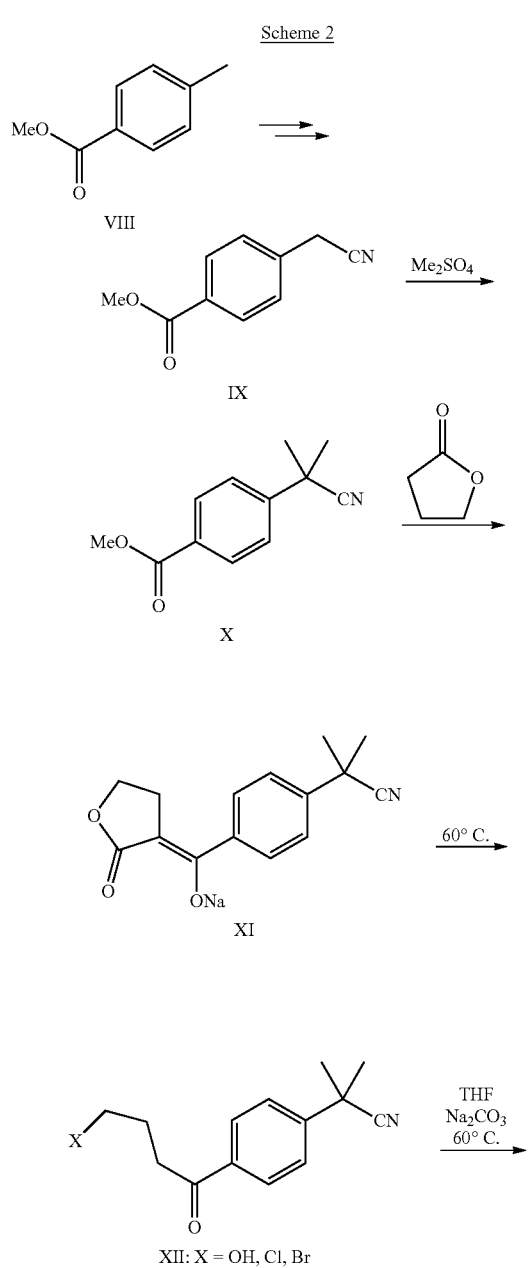

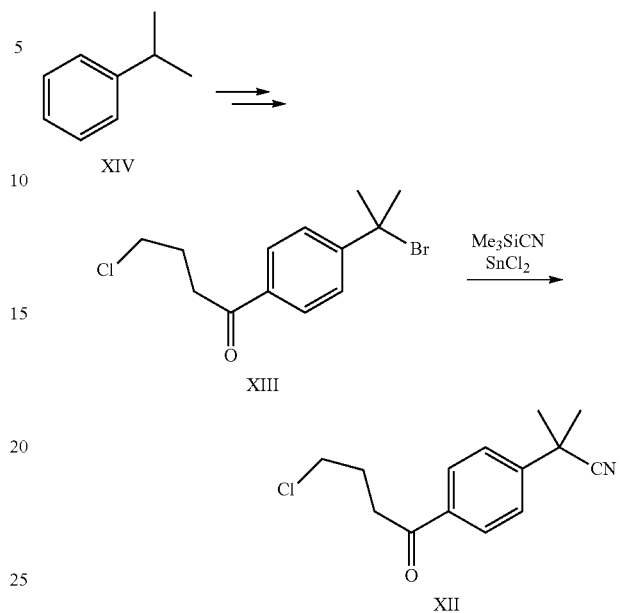

An alternative synthesis of intermediate XII (X=Cl) is also described in Example 6 of U.S. Pat. No. 6,340,761, starting from the intermediate of formula XIII, prepared from cumene (XIV) in 2 steps (examples 1 and 4). This is summarized in Scheme 3 below.

While a general a 4 step process towards compound of formula I as described in Scheme 3 is possible, the conditions for conversion of a tertiary bromide of formula XIII into the tertiary nitrile of formula I are very demanding and lack industrial applicability due to an expensive, volatile and highly toxic cyanide source and need of stoichiometric quantities of a toxic tin compound.

Another approach towards the compound of formula XII is described by Di Giacomo et al. in Farmaco 1999, 54, 600-610. Starting from (4-bromo-phenyl)-2,2-dimethyl-acetonitrile (formula XV) the compound of formula XII was obtained utilizing several palladium-catalysed steps involving stannylation with the trishexabutyl tin-dimer and acylation with 4-chlorobutyryl chloride (scheme 4). Again compound XV is not a readily available commodity and needs to be prepared from precursors like p-bromo-toluene XVI, by analogous hazardous operations as mentioned in schemes 1 and 2.

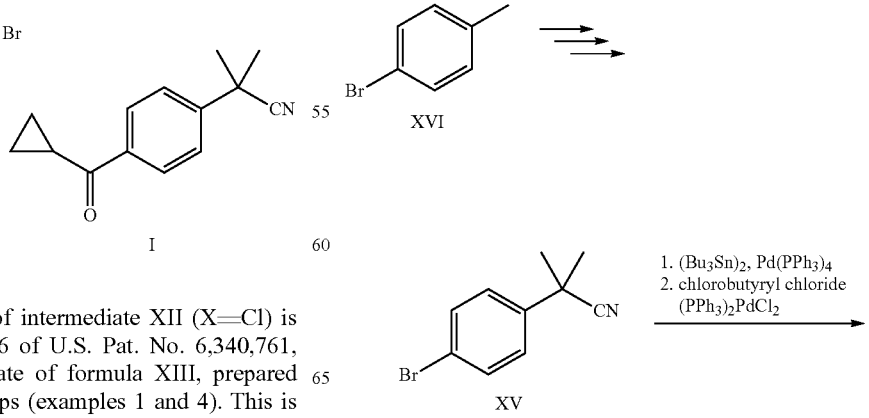

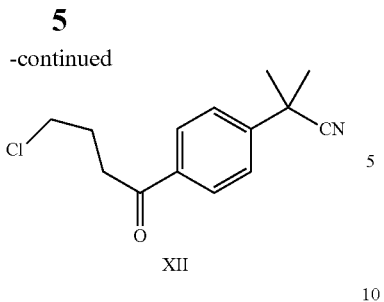

Finally, another approach towards 2-[4-(cyclopropanecarbonyl)phenyl]-2-methyl-propanenitrile of the formula I is shown in a general scheme of U.S. Pat. No. 6,340,761 (scheme E, columns 37/38, steps h and o) and outlined in scheme 5.

Scheme 5

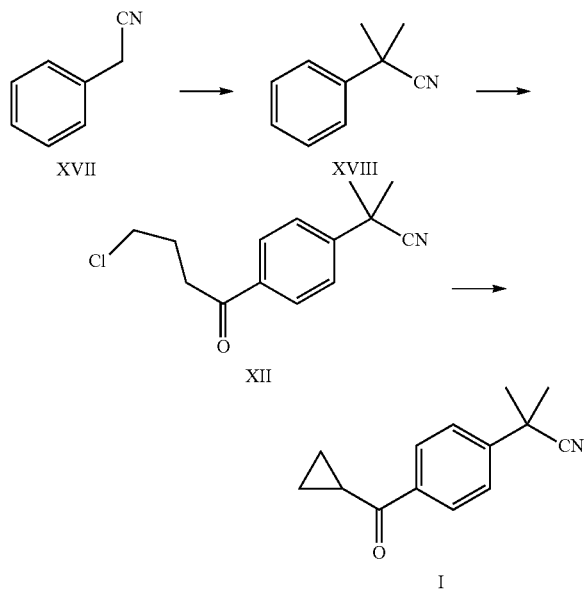

Starting from benzyl nitrile XVII, dialkylation should furnish the intermediate of formula XVIII. Subsequent Friedel-Crafts-acylation with 4-chlorobutyryl chloride and cyclisation should furnish key intermediate I in a very short 3-step sequence. Unfortunately, the reactions are not described as experimental examples. An experimental verification of the reaction showed that the reaction of dimethyl-phenyl-acetonitrile of formula XVIII with 4-chlorobutyryl chloride using several variations of the Friedel Crafts acylation performed poorly. At best, the product obtained after cyclisation contained the compound of formula I in about 40% whereas the major product (about 60%) is the undesired meta-isomer of formula XIX as shown in Scheme 6 and described in reference example 1.

Scheme 6

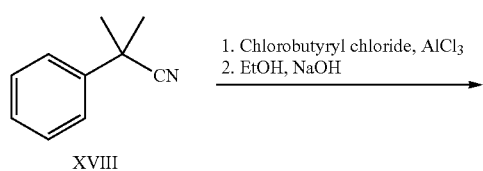

1. Chlorobutyryl chloride, AlCl$_3$
2. EtOH, NaOH

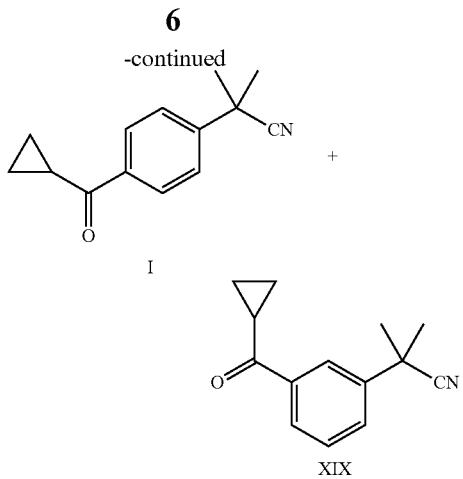

In summary, all of the different approaches towards the desired target 2-[4-(cyclopropanecarbonyl-)-phenyl]-2-methyl-propanenitrile of the formula I as described in Schemes 1-6 above, make use of either long chemical sequences (4-5 steps) which use hazardous, highly toxic and expensive reagents (Schemes 1-4) or suffer from low yielding and unselective chemical transformations (Scheme 5-6).

Definitions

The term (C1-C18)alkyl means a straight or branched hydrocarbon chain. The carbon chain is straight-chain or branched and comprises 1 to 18 carbon atoms, for example methyl, ethyl, n-propyl, isopropyl, n-butyl, isobutyl, tertbutyl, pentyl, isopentyl, neopentyl, hexyl, 2,3-dimethylbutyl, neohexyl, nonyl, dodecyl or octadecyl.

The term (C2-C17)alkenyl or (C3-18)alkenyl, respectively, means hydrocarbon radicals whose carbon chain comprises 2 or 3 to 17 or 18 carbon atoms, respectively and, depending on the chain length, is straight-chain or branched and has 1, 2 or 3 double bonds, for example vinyl, 2-propenyl, isopropenyl, isobutenyl, butenyl, or heptadec-8-enyl. The double bond may be arranged in the E or Z configuration. The double bonds may be both internal and terminal.

Halogen means fluoro, chloro, bromo or jodo.

SUMMARY OF THE INVENTION

It is an object of the present invention to provide an alternative process for the preparation of 2-[4-(cyclopropanecarbonyl-)-phenyl]-2-methyl-propanenitrile (formula I) starting from commercially available materials or compounds described already in the literature, themselves being prepared easily from commercially available materials, by using simple and environmentally compatible reagents and solvents, to afford the compound of formula I in a good overall yields and good purity with a short chemical synthesis.

The above object is achieved by starting with commercially available compounds such as fluoro- or chlorobenzene, chlorobutyryl chloride (for preparing compound of formula XX), isobutyronitrile and a base. The compound of formula I can be prepared in 3 synthetic steps starting from fluoro- or chlorobenzene.

The present invention relates to a novel process for preparing 2-[4-(cyclopropanecarbonyl-)-phenyl]-2-methyl-propanenitrile of the formula I comprising reacting cyclopropyl-(4-fluoro or chlorophenyl)methanon of formula XX (R1 is F or Cl) with isobutyronitrile of formula XXI using a suitable base to yield the compound of formula I (scheme 7).

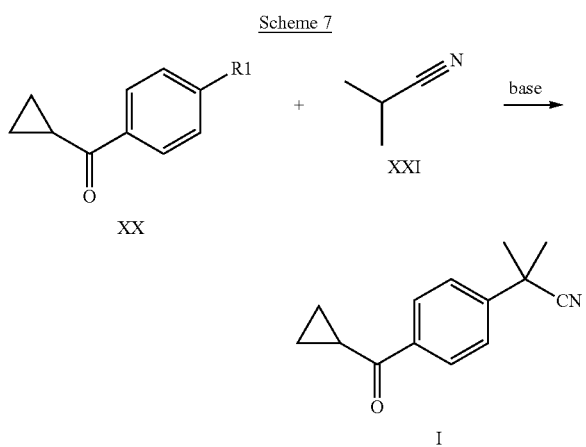

DESCRIPTION OF RELATED ART

The conversion of aryl fluorides to tertiary nitriles is known from the literature as nucleophilic aromatic substitution ($S_{N_{Ar}}$), first described by Caron et al. (J. Am. Chem. Soc. 2000, 122, 712 or in U.S. Pat. No. 6,303,782, Pfizer Inc.) and references cited therein. The acidic position alpha to the nitrile is deprotonated by the base potassium hexamethyldisilazane (KHMDS) and the carbanion of the nitrile reacts with the fluoroaromatic compound by displacement of the fluoride leaving group—known as $S_{N_{Ar}}$. Fluoride is usually much more preferred over other halogens due to the higher reactivity in the aromatic substitution reaction. Caron et al. reacted different substituted aryl fluorides of formula XXII wherein R4=OMe, Cl, H, $CF_3$ or CN, with certain secondary nitriles in the presence of the base KHMDS in toluene or THF, to obtain tertiary arylnitriles of formula XXIII according to scheme 8.

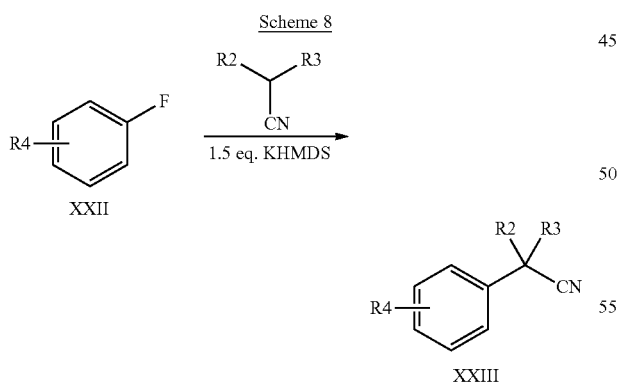

The only base used successfully was KHMDS. Other bases such as NaHMDS, LiHMDS gave poor yields or no conversion at all ($Cs_2CO_3$, KOtBu, LDA).

Indeed KHMDS seems to be the preferred base and these reaction conditions are widely used in the literature (J. Org. Chem. 2013, 78, 1222 and references cited therein).

However, a corresponding conversion of compounds of formula XXII containing an ester, ketone or aldehyde substituents in R4 is not described in the literature. This is consistent with the knowledge that the addition to the carbonyl group in such substituents is more facile than the displacement of the fluoride in a nucleophilic aromatic substitution resulting in more side products.

For example, the addition of a nitrile-carbanion to the carbonyl group is well known and described for instance in U.S. Pat. No. 5,059,615 (Bayer AG, Example 19), wherein the 1,2-addition of the cyclopropyl nitrile anion to the carbonyl in the N-methoxy-N-methyl-amide of p-fluorobenzoate took place rather than fluoride displacement. In another example, reported by Kauffmann et al. (Chem. Ber. 1992, 125, 899 and 907), different α-metalated secondary nitriles (M=Li, Fe, Ti, Cr, Co, Cu) were added to several aldehydes and ketones and secondary and tertiary alcohols were the products. In another example, described in published patent application US2012/0035122 (pages 29-31), an aromatic aldehyde function para to a fluoride had to be masked as a diethyl acetal (reaction of 40 with 41 using KHMDS), in order to allow the nucleophilic aromatic substitution of the fluoride instead of the addition into the carbonyl.

Accordingly, prior art suggests that the addition of isobutyronitrile to cyclopropyl-(4-fluorophenyl)methanon of formula XXa would take place by reacting with the carbonyl group and not by aromatic nucleophilic substitution shown in Scheme 7.

In line with these expectations, it was found that addition of isobutyronitrile anion, prepared from LiHMDS and isobutyronitrile, to a compound of formula XXa gave solely the expected addition product of formula XXIV as shown in scheme 9 and not one of the two other compounds of formula I and XXV (confirmed in reference example 2 herein below).

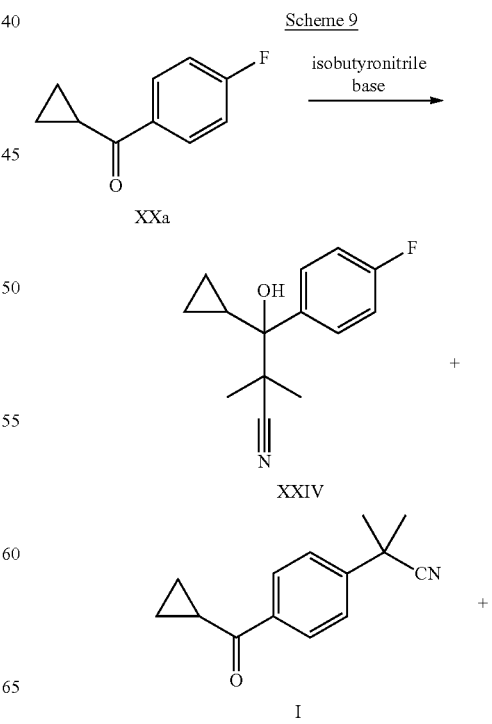

-continued

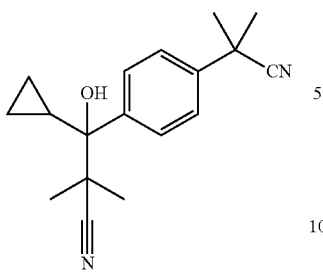

XXV

DETAILED DESCRIPTION OF THE INVENTION

Despite all the negative findings in the art it has been found that the conversion of a compound of formula XX into the compound of formula I can be achieved by the process of the present invention.

In one embodiment the present invention relates to a process for the preparation of the compound of formula I

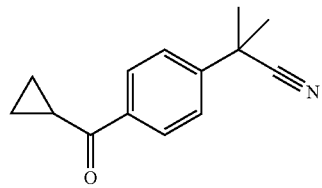

I comprising reacting a compound of formula XX

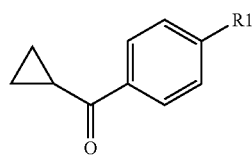

XX wherein R1 is fluoro or chloro,
with isobutyronitrile of formula XXI

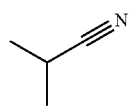

XXI in the presence of a suitable base.

Cyclopropyl-(4-fluorophenyl)methanon [CAS No: 772-31-6] of formula XXa

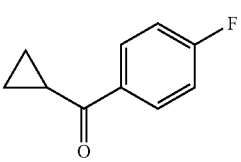

XXa can be prepared from fluorobenzene [CAS No: 462-06-6] in a 2 step synthesis, as described by Hannack et al. (Chem. Ber. 1963, 96, 2532-36) or Schliemann et al. (Pharmazie 1980, 35, 140).

Cyclopropyl-(4-chlorophenyl)methanon [CAS No. 6640-25-1] of formula XXb

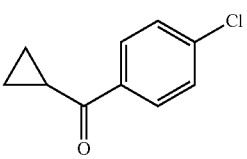

XXb can be prepared from chlorobenzene [CAS No. 108-90-7] in a 2 step synthesis, as described in the literature (Schliemann et al., Pharmazie 1980, 35, 140), This is similar to the transformation of the compound of formula III to the compound of formula V shown in scheme 1. Isobutyronitrile [CAS No: 78-82-0] is commercially available.

In one embodiment of the process of the present invention R1 is fluoro. In another embodiment of the process of the present invention R1 is chloro. Although substitution reactions of chloroaromatic compounds and alkylnitriles are known to require highly activated aromatics, such as a para nitro- or a cyano-substituent (see Makosza et al. in Tetrahedron 1974, 30, 3723 or Gorman et al. in Org. Biomol. Chem. 2011, 9, 2661), it has been found that in the process of the present invention the reaction also works for cyclopropyl-(4-chlorophenyl) methanon.

In an embodiment of the process of the present invention the base is potassium hexamethyldisilazane (KHMDS), sodium hexamethyldisilazane (NaHMDS) or sodium amide.

In one embodiment the base is used in an amount of 1 equivalent or more, i.e. an excess. The excess is not limited but for practical purposes is in the range of 1 to 10 equivalents. In another embodiment it is in the range of 1 to 5 equivalents. In a further embodiment it is in the range of 1 to 2 equivalents. Unless specified otherwise herein, the term "equivalents" refers to mol-equivalents.

In one embodiment the isobutyronitrile can be added in an amount of 1 equivalent or more, i.e. an excess. The excess of the nitrile is not limited but for practical purposes is in the range of 1 to 10 equivalents. In another embodiment it is in the range of 1 to 5 equivalents. In a further embodiment it is in the range of 2 to 4 equivalents.

The reaction of the compound of formula XX with the base and the isobutyronitril can be performed without any further solvent or in an aprotic solvent such as but not limited to xylene, benzene, toluene, THF and other ethers like MTBE or dimethoxyethane (DME). Preferred is toluene or xylene. The base may be added as such or, where desirable from a practical point of view, in a solvent. Even the isobutyronitrile reagent itself may be used as solvent. The amount of solvent is usually from 0.5 l to 6 l per kg of the compound of formula XX. The temperature used is ranging from 0° C. to 100° C. depending on the freezing point and the boiling point of the solvent and their mixtures, preferably at 20° C. to 60° C.

In one embodiment of the process of the present invention KHMDS is used as base. If KHMDS was used, the desired product of formula I was formed as the main product among the side product of formula XXV resulting from the concomitant addition into the carbonyl (see example 3). A yield of 80% of the compound of formula I was obtained at temperatures between 30-60° C., 4 equivalents of the nitrile and 1.5-2 equivalents of KHMDS.

In another embodiment of the process of the present invention NaHMDS is used as base. Commercial NaHMDS solutions are only available in lower concentrations (typically 0.6M in toluene, available e.g. from Sigma Aldrich). However a higher concentration is preferred for industrial scale application. NaHMDS is prepared from sodium and hexamethyldisilazane at high temperature and pressure with long reaction times (215° C., 6 bar, 16-24 h) as described in U.S. Pat. No. 5,420,322. Other bases like sodium hydride are also described, but again long reaction times (16 h) are required, even in a presence of activators like NaOtBu as described in J. of Organometallic Chem. 2010, 695, 2814.

However, higher concentrated NaHMDS solutions in toluene or xylene up to 2M can be prepared by a novel procedure in a short time. Thus in an embodiment of the process of the present invention the compound of the formula I is prepared according to scheme 7, wherein NaHMDS is prepared from sodium and an appropriate chloro aromatic compound, such as but not limited to chloro benzene or 2- or 4-chloro toluene, and hexamethyldisilazane in a suitable solvent.

Solvents which can be used for making higher concentrated NaHMDS-solutions are aprotic solvents such as but not limited to xylene, benzene, toluene, THF and other ethers like MTBE. Most preferred is xylene. The amount of solvent which can be used ranges from 2 l to 6 l, preferably 3 l, per kg of hexamethyldisilazane in order to obtain a high concentration. The temperature used is ranging from 0° C. to 140° C. depending on the freezing point and the boiling point of the solvent and their mixtures, preferably a temperature of 100° C. to 120° C. is used.

For preparing the NaHDMS-solution one equivalent or a slight excess of the chloro aromatic compound, one equivalent or a slight excess HMDS and two equivalents sodium are used. The reaction is fast and quantitative at elevated temperatures so that the concentration of NaHMDS, due to the stoichiometry of the reaction, is half of the initial sodium concentration. The reaction time ranges from minutes to several hours, depending on the nature of the chloroaromatic compound and the reaction conditions, like solvent and temperature.

The higher concentrated NaHMDS-solution can be used directly in the process of the present invention. Thus, for example, isobutyronitrile (XXI) and cyclopropyl-(4-fluorophenyl)methanon XXa is added successively to the NaHMDS-solution at 35° C. and the mixture is heated between 50-80° C. for 2-4 h. Good results (about 66%) were obtained with 1.5 eq. of NaHMDS, 2 equivalents of isobutyronitrile and 1 equivalent of compound XXa at 55° C. for 3 h.

Beside bases such as potassium hexamethyldisilazane (KHMDS) or sodium hexamethyldisilazane (NaHMDS) further bases can be used, especially if they are more convenient.

As the appropriate base has to be strong enough to deprotonate isobutyronitrile and enable nucleophilic aromatic substitution, a likely side reaction is the direct attack of the base in a nucleophilic aromatic substitution. This reaction is expected to be prevalent for sterically less demanding bases. However, even sterically hindered potassium tert-butoxide leads to direct nucleophilic aromatic substitution and significant amounts (up to 60%) of the side product of formula XXVI were identified as a result of the fluoride displacement in the compound of formula XX by the tert-butoxy group.

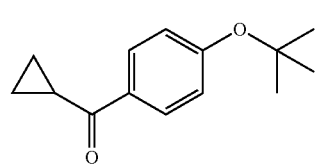

XXVI

Although this facile direct nucleophilic aromatic substitution with sterically less encumbered bases is expected, it has unexpectedly found that sodium amide can be used to achieve the desired conversion. Sodium amide has the advantage to be a commodity available in bulk and its use avoids some of the issues associated with hexamethyldisilazane based bases.

Thus in a further embodiment of the process of the present invention the compound of formula I is prepared, wherein sodium amide is used as base in the preparation of the compound of formula I.

In the reaction each of the components can be used with one equivalent or in an excess, for example 1.0 to 2.0 equivalents of $NaNH_2$ and 1.5-5.0 equivalents of isobutyronitrile relative to compound of formula (XX).

With sodium amide the formation of the compound of formula I proceed without the formation of major side-products. However, the conversion of the compound of formula XX stops at about 50%.

It is known that kinetics of reactions employing sodium amide, such as elimination of HX (X=Br, Cl) of dibromocyclohexane or alkyl- or methoxy-substituted bromoaromatics, can be improved by using so called "complex bases", described by P. Caubere in Chem. Rev. 1993, 93, 2317 or in Synth. Comm. 1989, 19, 3323). These complex bases are prepared either from sodium amide/ tert-butanol or sodium amide/diethylene glycol monoethylether with a ratio of 2:1 in polar aprotic solvents such as tetrahydrofurane (THF) or dimethoxyethane (DME). However, the utilisation of the complex bases derived from alcohols as described by Caubere gave not satisfying results in the present reaction. No desired nucleophilic aromatic substitution to prepare product I was observed with tert-butanol as activator and only side products were observed, such as compound of formula XXVI (2%). Only 10% of the product I were formed with the complex base $NaNH_2$/diethylene glycol monoethylether and more than 50% of the corresponding unwanted ether of formula XXVII was observed.

XXVII

Nevertheless, it has been found that the overall yield of the substitution reaction can indeed be further increased in general by adding a reagent which activates and accelerates the reaction.

Accordingly, in a further embodiment of the process of the present invention the compound of formula I is prepared wherein a compound comprising at least 3 —$CH_2$—CH(R7)-O— units, wherein R7 is H or $CH_3$, is added to the reaction mixture comprising the methanon XX, the isobutyronitril and the base. R7 being H or CH3 in one unit is independent of R7 in each other unit. In one embodiment R7 is H, i.e. all R7 are H. In another embodiment R7 is $CH_3$.

Such a compound containing these units is hereinafter referred to as a "polyether". The units in such a polyether can be consecutive, i.e. in a row, such as in a polyethylene glycol, or partially separated, such as in an aza-crown ether or in dendrimer like compounds.

It has unexpectedly been found that various types of such polyethers can be added and result in a complete conversion of the compound of formula XXa to give compound of formula I as shown in Scheme 7 in a higher yield than with the base alone. In one embodiment a polyether comprising at least 4 units is added. In a further embodiment a polyether comprising at least 5 units is added. In a further embodiment such units are connected with each other in a chain.

The polyether additive can be any compound comprising the mentioned oxy-ethylen or propylene based units. Such polyethers are known to a person skilled in the art. Examples for various embodiments of such compounds are further described below and in the examples in more detail without limiting it to them.

In one embodiment of the process of the present invention the added compound containing the above mentioned $CH_2$—CH(R7)-O— units is a polyethylene glycol (PEG) or polypropylene glycol (PPG) of the formula HO($CH_2$—CH(R7)-O)nH, wherein R7 is H or CH3, or a mixture thereof, which is unsubstituted or substituted at one or both ends. The number of units is defined by n.

A mixture means that either PEGs and PPGs are synthesized separately and are mixed together to form a mixture or that in the synthesis of the polymer itself the polymerisation is done in a manner that a polymer molecule contains PEG as well as PPG units. These kinds of molecules are called copolymers.

The number (n) of units in such a polyether, esp. in the PEG and PPG, is not limited and can range from 3 to 200 000 units and the upper limit is only depending on the structure and availability of the corresponding polyether.

The amount of the polyether can vary over a broad range. It can be used in stoichiometric amounts relative to the compound of formula XX. However, it has unexpectedly been found that for the process of the present invention the amount of the polyether added can be less than stoichiometric on a molar level.

Due to the various molecular weights of compounds containing the above mentioned —$CH_2$—CH(R7)-O— unit, which can range from several hundred to several million in large polymers, mass equivalents instead of mol equivalents are used in the following for easier description and comparison.

In one embodiment of the process of the present invention, the polyether compound is added in the range of from 0.02 to 0.50 mass equivalents relative to compound of formula XX depending on the structure of the polyether. In a further embodiment the poylyether is added in the range from 0.02 to 0.30 mass-equivalents. In yet another embodiment the polyether is added in the range from 0.02 to 0.2 mass equivalents.

In one particular embodiment of the process of the present invention the compound of formula I is prepared, wherein a compound of formula XXVIII R6O($CH_2$—CH(R7)-O)nR8    XXVIII wherein n is 3-200 000, R6 and R8 are, independently of each other, H, (C1-C18) alkyl, (C3-C18) alkenyl, phenyl, —$CH_2$-phenyl, 2-aminopropyl, 3-sulfopropyl, glycidyl or C(=O)R9, R7 is, independently of each unit, H or $CH_3$, and R9 is (C1-C17)alkyl, (C2-C17) alkenyl, or phenyl, wherein phenyl is unsubstituted or substituted by one or two groups independently selected from (C1-C12)alkyl and halogen, is added to the reaction mixture comprising the methanon XX, the isobutyronitril and the base.

The following general remark applies to all polymers further defined below. All these are polymers having the mentioned units in row and the mentioned number n of the —($CH_2$—CH(R7)O)— units in the material used describes the average value denoting the largest portion of such molecules in the mixture which mixture also contains molecules with more or less units in lower amounts. This is due to the synthesis process and purification process. The corresponding distribution of the various molecules in a certain polyether is either specified in the data sheet of the suppliers or can be determined by several analytical methods such as mass spectroscopy. The number n and the corresponding molecular weight of the polymer apply equally and the n and the molecular weight values can be used interchangeably.

An alternative description of the above unit in such a polyether, which can also be seen in product descriptions, is that the unit incl. the remainder of the polymer is turned around by 180° resulting in R8(O—CH(R7)-$CH_2$)nOR6. Even sometimes the brackets are shifted by one position and the unit looks like —(O—$CH_2$—CH(R7))nO—.

Moreover, different substituents have been allocated to the ends of the polymer (R6 and R8). This is only to better describe the situation in a molecule, if the ends are differently substituted, although in practice the products are usually identical if the two substituents are exchanged and if the polymer is optionally drawn up differently as explained above. Therefore, the corresponding situation, wherein the substituents are exchanged, is encompassed as well by this definition. For example, if R6 is H and R8 is methyl, the corresponding definition, wherein R6 is methyl and R8 is H, is encompassed as well.

As defined above in a compound of formula XXVIII R7 in one unit is independent from R7 in another unit and thus may be the same or different in the next following oxy-ethylene unit.

In one embodiment thereof R7 is H resulting in a compound of the formula

R6O($CH_2$—$CH_2$—O—)nR8    XXVIIIa which can be regarded as a polyethylene glycol (PEG) derivative.

In another embodiment of the compound of formula XXVIII R7 is CH$_3$. This results in a compound of the formula

R6O(CH$_2$—CH(CH$_3$)—O)$n$R8  XXVIIIb which can be regarded as a polypropylene glycol (PPG) derivative.

Sometime such a polypropylene glycol is drawn up as follows by shifting the brackets

R6(OCH$_2$—CH(CH$_3$))$n$-OR8

However, this does not change the overall structure of the compound as long as the substituents in R6 and R8 are identical.

R6 and R8 in a compound of formula XXVIII can be the same or be different, such as, for example, R6 being COR9 and R8 being an alkyl group. The alkyl in R6 and R8 can have the same or different meanings, i.e. the length of the alkyl groups can be different at each end.

In one embodiment R6 and R8 in formula XXVIII are, independently of each other, H; (C1-C18)alkyl, such as methyl (Me), ethyl (Et), butyl (Bu), dodecyl, or octadecyl; (C3-C18)alkenyl, such as allyl or (Z)-9-octadecenyl; glycidyl; phenyl; 2-aminopropyl or COR9.

In one embodiment R6 and R8 in formula XXVIII are, independently of each other, H, (C1-C18)alkyl, (C3-C18) alkenyl, 2-aminopropyl or COR9. In a further embodiment R6 and R8 are, independently of each other, H or (C1-C18) alkyl, (C3-C18)alkenyl or 2-aminopropyl. In one further embodiment R6 and R8 are, independently of each other, H or (C1-C18)alkyl or (C3-C18)alkenyl. In a further embodiment, R6 and R8 are, independently of each other, H or (C1-C12)alkyl. In a further embodiment, R6 and R8 are, independently of each other H or (C1-C6)alkyl. In a further embodiment, R6 and R8 are, independently of each other H or methyl.

In an embodiment of the compound of formula XXVIII R8 is H and R6 is as defined in the various embodiments in the foregoing paragraphs but not H. Such as by way of example R8 is H and R6 is (C1-C18)alkyl or (C3-C18) alkenyl.

In a further embodiment of the compound of formula XXVIII both R6 and R8 are, independently of each other, as defined in the various embodiments in the foregoing paragraphs but are not H. In one embodiment both R6 and R8 are (C1-C18)Alkyl.

In an embodiment of the compound of formula XXVIII R6 and R8 are H.

In an embodiment of the compound of formula XXVIII R9 is (C1-C17)alkyl, vinyl, 2-propenyl, heptadec-8-enyl or phenyl, wherein phenyl is unsubstituted or substituted by one or two groups independently selected from (C1-C12) alkyl and halogen In a further embodiment of R6, R8 or R9 phenyl is substituted by or or two, preferably one, (C1-C12)alkyl groups. In a further embodiment phenyl is unsubstituted.

There is no limit in the maximum length of the PEG or PPG for performing the reaction itself and the largest one may be used in the reaction. A limitation may only be in the practical use of such compounds, especially the work-up at the end of the reaction, due to the emulsifying character of such molecules or the synthetic availability.

In a particular embodiment of a compound of XXVIII n=4-200 000. This corresponds in case of a PEG based compound to a polyethylene glycol having an average molecular weight of about 200 to 8,000,000. In one embodiment a PEG or PPG is used wherein n is 5 to 5000. In another embodiment n is 5 to 1 000. In a further embodiment n is 5 to 100.

As mentioned before R7 is, independently of each other, in the various units H or CH$_3$. Thus, this can result in a compound wherein all R7 are H or all R7 are CH$_3$ as described above.

However, in a further embodiment of the compound of formula XXVIII in one or more of the n oxy-ethylene units R7 is H and in one or more R7 is CH$_3$. This corresponds to a polyether containing oxy-polyethylene as well as oxy-polypropylene units. Such a polymer, wherein e.g. one or more consecutive units, wherein R7 is H, are followed by a number of consecutive units, wherein R is CH$_3$, is called a block-copolymer. Accordingly, by way of example a PEG-PPG diblock-copolymer or a PEG-PPG-PEG triblock copolymer or any other combination may be used.

The above embodiments and further embodiments of a compound of formula XXVIII are further described below.

In one embodiment the compound of formula I is prepared according to the process of the present invention, wherein in the compound of formula XXVIII R7 is H. in this case a polyethylene glycol based compound is used. In this embodiment, R7 is H and R6 and R8 are H in the compound of formula XXVIII.

This corresponds to a polyethylene glycol (PEG) of formula XXXI

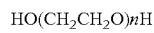HO(CH$_2$CH$_2$O)$n$H  XXXI

In a particular embodiment thereof the average value of n=3-200 000. This corresponds to a polyethylene glycol having an average molecular weight of about 200 to 8,000, 000. However, there is no limit in the maximum length of the PEG and any size may be used for the reaction. However, for practical purposes, especially the work-up at the end of the reaction, the size of the PEG useful is limited. In one embodiment a PEG is used wherein n is 5 to 5000. In another embodiment n is 10 to 1 000. In one embodiment n, and the corresponding PEG, is 11 (PEG 500), 20 (PEG 1000), 35 (PEG 1500), 45 (PEG 2000), 70 (PEG 3000), 75 (PEG 3350), 80 (PEG 3500), 90 (PEG 4000), 450 (PEG 20 000), 23000 (PEG 1 000 000), or 200 000 (PEG 8 000 000). In another embodiment the PEG is in range from an average n=20-90 (molecular weight 1000-4000). In a further embodiment n is 35-90 (PEG 1500-4000).

It has been found that different PEG's of formula XXXI can be used in non-stoichiometric (catalytic) amounts in the process of the present invention. Typically 0.02-0.2 mass equivalents of PEG with respect to the compound of formula XX can be used, depending on the molecular weight of the PEG. For instance 0.075-0.15 mass equivalents of PEG1000 (with n~20) [25322-68-3] were needed for complete conversion of a compound of formula XXa as shown in scheme 7.

In this embodiment analysis of the reaction mixture revealed that PEG is reacting first with the compound of formula XX as shown in scheme 10 and a diaryl-PEG compound of formula XXXII is prepared in situ by nucleophilic aromatic substitution Scheme 10

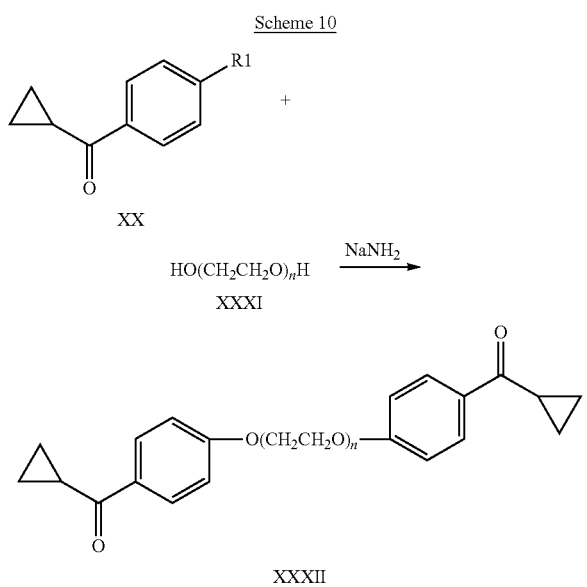

After conversion of XXXI to compound XXXII, the residual amount of compound XX is converted into compound I as shown in scheme 7 wherein the side product XXXII is accelerating the reaction in the overall substitution of remaining XX by isobutyro nitrile. Therefore compound XXXI is used only in low amounts, especially if the number of n is small (n is 4 to 7), in order to minimize this side reaction and formation of side product XXXII. Formation of the side product of formula XXXII wherein n is 9 (XXXIIa) is described in Example 8.

In a further embodiment the compound of formula I is prepared according to the process of the present invention, wherein in the compound of formula XXVIII R7 is H, R8 is H and R6 is as defined in the various embodiments above but not H. This corresponds to a mono substituted polyethylene glycol (PEG) for which by way of example a compound of formula XXXIII R6O(CH$_2$CH$_2$O)$n$H        XXXIII is shown.

The compound of formula XXXIII is reacting with a compound of formula XX similar as described for scheme 10 yielding a compound for formula XXXIV as shown in scheme 11.

Scheme 10

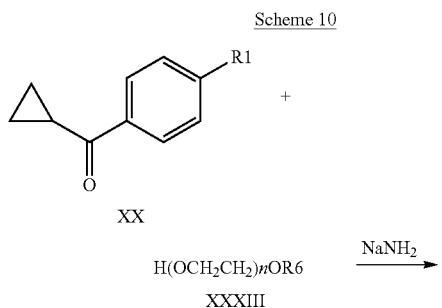

-continued

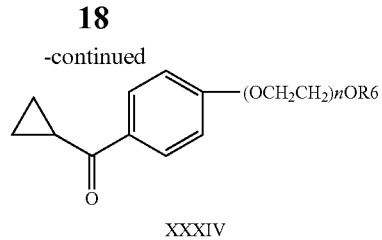

XXXIV

The average molecular weight is depending on the nature of the group R6, but is typically in the same range as for the unsubstituted PEG described before. Especially for the long PEG molecules the R6 does not add much to the overall molecular weight. In an embodiment mono substituted PEG's of formula XXXIII can be used wherein the molecular weight is varying from 300-5000 depending on the nature of R6. Those are commercially available (e.g. Sigma Aldrich). For instance with 0.15 mass-equivalents of polyethylene glycol (n is 20) and substituted with R6=C18H35 (MW 1150, CAS: 9004-98-2, Brij® O20) the compound of formula I was obtained in 81% yield according to scheme 7 (Example 17q herein below).

In a further embodiment the compound of formula I is prepared according to the process of the present invention, wherein in the compound of formula XXVIII R7 is H and R6 and R8 are, independently of each other, as defined in the various embodiments of R6 and R8 above but are not H. Such a compound is designated disubstituted-PEG and corresponds to a compound of the formula R6O(CH$_2$—CH$_2$O)$n$R8        XXXVI Examples of compounds showing the broad range of substituents is PEG substituted by R8 Acrylate and R6 is Phenyl (CAS 56641-05-5, MW 324) or PEG wherein the R6 substituent is para-nonylphenyl and R8 is 3-sulfopropyl (CAS: 119438-10-7, n~20)

In a particular embodiment of a compound of formula XXVI R7 is H and R6 and R8 are methyl. In one embodiment n=10-44 corresponding to a molecule weight of about 500 to 2000, respectively. In another embodiment n is varying from n=10 (molecular weight about 500) to n~20 (molecular weight about 1000).

The various substituted PEG's of formula XXXIII and XXXVI can be used as described above for PEG in low amounts as activator in the process of the present invention. Typically 0.02-0.3 mass equivalents of mono-substituted PEG are added, depending on the molecular weight of the PEG to catalyse the reaction according to scheme 7. A disubstituted, especially, a dialkylated, PEG is added in a range from 0.02 to 0.50 mass equivalents with respect to the compound of formula XX depending on the molecular weight of the PEG. For instance adding 0.1 mass equivalents of dimethyl-PEG500 [CAS No. 24991-55-7] with respect to the compound of formula XX yields complete conversion of a compound of formula XXa into a compound of formula I according to scheme 7.

In a further embodiment of the process of the present invention the compound of formula I is prepared according to the process of the present invention, wherein in a compound of formula XXVIII R7 is CH$_3$, R6 is H and R8 is H.

This corresponds to a polypropylene glycol (PPG) of formula XXXIII

HO(CH$_2$CH(CH$_3$)O)$n$H        XXXVII

The number of n and thus the molecular weight can range over a broad range as described for the PEG compounds before.

Different PPG's of formula XXXVII can be used as described above for PEG as activators in the process of the present invention. PPG's which can be used are varying from 250-8000 molecular weight with n=4-140 and are commercially available (Sigma Aldrich).

PPG is added in a range from 0.02 to 0.20 mass equivalents with respect to the compound of formula XX depending on the molecular weight of the PPG.

In a further embodiment of the process of the present invention the compound of formula I is prepared according to the process of the present invention, wherein in a compound of formula XXVIII R7 is $CH_3$, R8 is H and R6 is as defined in the various embodiments above.

This corresponds to a mono substituted polypropylene glycol (PPG) of formula XXXVIII

R6O(CH$_2$CH(CH$_3$)O)$n$H          XXXVIII

The number of n and thus the molecular weight can range over a broad range as described for the PEG or mono-substituted PEG compounds before.

Different mono substituted PPG's of formula XXXVIII can be used as described above for mono substituted PEG's of formula XXXIII. Mono substituted PPG's of formula XXXVIII which can be used are varying from 300-5000 in molecular weight depending on the nature of R6 and are commercially available (e.g. Sigma Aldrich). In one embodiment n is 4-100 and R6 is (C1-C4)alkyl, For instance, in one embodiment thereof, PPG-mono butylether 2500 (R6 is $C_4H_9$, n is ~40, CAS: 9003-13-8) can be used (see Example 17j).

In a further embodiment, the compound of formula I is prepared according to the process of the present invention, wherein in a compound of formula XXVIII R7 is $CH_3$ and R6 and R8 are, independently of each other, as defined in the various embodiments above but are not H. This corresponds to a disubstituted-polypropylene glycol of formula XXIX

R6O(CH$_2$CH(CH$_3$)O)$n$R8          XXXIX

In one embodiment R6 or R8 in formula XXXIX is (C1-C6)alkyl such as methyl (Me), ethyl (Et), propyl (Pr), butyl (Bu) or hexyl (Hex), allyl (All), benzyl (Bn), glycidyl or is a C(O)R9 ester group. In a special part of this embodiment R6 and R8 in compounds of formula XXXIX are not equal, such as but not limited to an ester and an alkyl group. In one embodiment R6 and R8 are methyl or ethyl. In a further embodiment R6 and R8 are methyl.

In one embodiment a disubstituted-PPG of formula XXXIX is used wherein R6 and R8 are methyl and n=4-30 corresponding to a molecule weight from about 300 to 2000, respectively. In another embodiment n is varying from n=4 (molecular weight about 300) to n~16 (molecular weight about 1000).

The various PEG's and PPG's described above as well as the copolymers thereof further described below are commercially available or can be prepared by methods known in the art. Basically polyethylene glycol can be produced by the reaction of ethylene oxide with water, ethylene glycol, or ethylene glycol oligomers. The reaction is catalyzed by acidic or basic catalysts. Similar polypropylene glycol is produced by ring opening polymerization of polypropylene oxide starting with an alcohol such as 2-hydroxy-1-propanol. The polymer chain length depends on the ratio of reactants. Using different reactants during the polymerization copolymers of PEG and PPG can be made as well. For mono substituted derivatives the polymerization can be started e.g. with a suitable R6-OH derivative, such as for example an (C1-C6)alkanol. For disubstituted (end-capped) polymers an R8 derivative may be used having a reactive group such as a bromo or chloro as in methyl chloride or methyl bromide, which allows the facile substitution with the hydroxyl group. Alternatively, dialkylated polyethylene glycol derivatives can be obtained by applying an end-capping on both ends of a polyethylene glycol polymer such as described in J. of Org. Chem. 1999, 64, 6870-6873. Similar, the preparation of dialkylated polypropylene glycol derivatives by end-capping of the polypropylene glycol is described by Idoux et al. (J. Chem. Eng. Data 1994, 39, 261-265). Many PEG, PPG or copolymers thereof of various length and having different substituents at one or both ends are commercially available from suppliers such as from Sigma Aldrich, Clariant or Dow Chemical.

The various PPG's of formula XXXVIII and XXXIX can be used as described above for the corresponding PEG in catalytic amounts in the process of the present invention. In one embodiment 0.02-0.3 mass equivalents of a monosubstituted PPG are added with respect to the compound of formula XX, depending on the molecular weight of the PPG in the reaction according to scheme 7. A disubstituted PPG is added in a range from 0.02 to 0.50 mass equivalents depending on the molecular weight of the PEG.

Moreover, the mentioned PEG's of formula XXVIIIa and PPG's of formula XXVIIIb can be used either alone or in a mixture thereof. Moreover, as mentioned before, R7 in a compound of formula XXVIII can be H in one unit and methyl in another, which results in a mixture of such units in the same polyether. These polyethers may also be further substituted at the ends. Accordingly, in a further embodiment of the process of the present invention mixtures of PEG/PPG are used as additive. Suitable compounds which can be used are for example PEG-PPG-PEG triblock copolymers of structure XXXVIa (CAS: 9003-11-6) with an average molecular weight from about 1000-15000 (see Example 17o), or PPG-PEG-PPG-triblock copolymers of structure XXXVIb with R6,R8=H or captured by a bis-2-aminopropylether (R6,R8 is 2-aminopropyl, Jeffamine®, CAS: 65605-36-9) with an average molecular weight from 500 to 2000 (see Example 17p), PEG-ran-PPG [CAS: 9003-11-6, ran: non defined order) with an average molecular weight from about 2500-12000, diblock-copolymers of PEG and polyethene (PE) (CAS: 251553-55-6) with an average molecular weight from about 600-2500 can also be used. All compounds are commercially available (Sigma Aldrich).

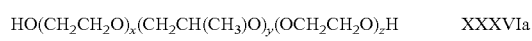

HO(CH$_2$CH$_2$O)$_x$(CH$_2$CH(CH$_3$)O)$_y$(OCH$_2$CH$_2$O)$_z$H          XXXVIa

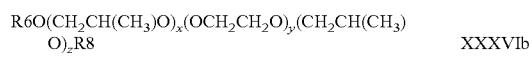

R6O(CH$_2$CH(CH$_3$)O)$_x$(OCH$_2$CH$_2$O)$_y$(CH$_2$CH(CH$_3$)O)$_z$R8          XXXVIb with x=0-100, y=0-100, z=0-100

In a further embodiment of the process of the present invention mixtures of mono substituted PEG/PPG are added. For example but not limited PEG-ran-PPG-monobutylether [CAS: 9038-95-3) with an average molecular weight from about 1000-4000 can also be used. All compounds are commercially available (Sigma Aldrich).

The various mixed PEG/PPG's can be used as described above for PEG in catalytic amounts in the process of the present invention. In one embodiment 0.02-0.3 mass equivalents of PEG/PPG-mixtures are added, depending on the molecular weight of the PEG/PPG-mixture, in the reaction according to scheme 7.

In a further embodiment, the compound of formula I is prepared according to the process of the present invention, wherein a cyclic polyethylene glycol (CPG) of formula XXXII

(—CH$_2$CH$_2$O—)$_n$          XXXXII n is 4-8, wherein one or more CH2-CH2 groups, preferably one or two, may be replaced by phenyl or cyclohexyl, is added.

Such cyclic polyethylene glycols (CPG) of formula XXXII are known as crown ethers and can also be used in the same manner and in the low amounts as described for PEG above. One is example is 12-crown-4 (see Example 17e)

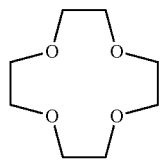

12-Crown-4

As indicated CPG's can be used wherein one or more, preferably one or two, PEG-units are replaced by a another diol like 1,2-benzenediol or 1,2-Cyclohexanediol as shown.

With 1,2-cyclohexanediol such CPG's are designated Dicyclohexano-crown ethers and one with two 1,2-cyclohexanediols is for instance

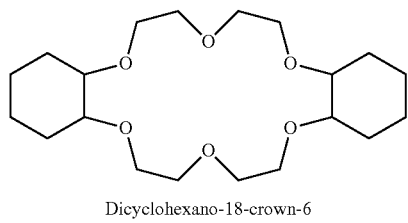 [SMILES: C1CCC2OCCOCCOC3CCCCC3OCCOCCOC2C1]

Dicyclohexano-18-crown-6

(CAS: 16069-36-6, can be purchased from VWR or Sigma Aldrich, see Example 17g).

In one embodiment a CPG is used wherein no CH2-CH2 group is replaced. In a further embodiment the crown-ether is selected from the group of 12-crown-4, 15-crown-5, 18-crown-6, dicyclohexano-18-crown-6 and dibenzo-18-crown-6.

In another embodiment CPG's of formula XXXXII can be used in the process of the present invention where one or more, preferably 1 or 2, of the oxygen atoms is replaced by a nitrogen atom, which nitrogen atoms may be further substituted or both may be connected via a further polyether chain. In one embodiment 2 oxygen atoms are replaced. In an embodiment thereof a compound having the general formula

XXXXIII

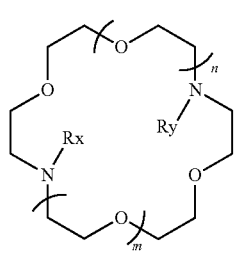

wherein n is 0, 1 or 2, m is 0, 1, 2

Rx and Ry are, independently of each other, H, (C1-C8) alkyl or benzyl, or

Rx and Ry together are —(CH$_2$CH$_2$—O)z-CH$_2$CH$_2$— with z=1, 2, is added.

Such compounds are designated aza-crown ethers. In one embodiment of a compound of formula XXXXIII, Rx and Ry are, independently of each other, H, (C1-C8)alkyl or benzyl. Examples of such ethers, are for instance but not limited to 4,13-Diaza-18-crown-6 (CAS: 23978-55-4).

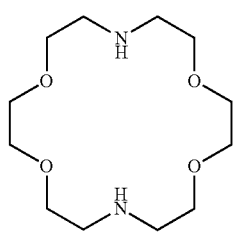 [SMILES: C1COCCOCCNCCOCCOCCN1]

One or more of the nitrogen atoms in aza-crown-ethers can be substituted with a benzyl group, such as in 1,10-Dibenzyl-1,10-diaza-18-crown-6 (CAS: 69703-25-9, see Example 17h).

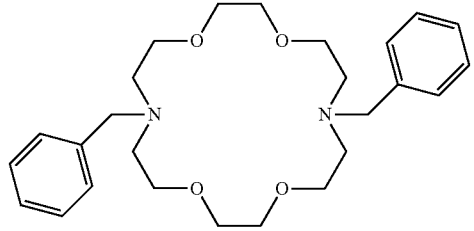 [SMILES: c1ccc(CN2CCOCCOCCN(Cc3ccccc3)CCOCCOCC2)cc1]

In the other embodiment of a compound of formula XXXXIII, Rx and Ry together are —(CH$_2$CH$_2$—O)z-CH$_2$CH$_2$— with z=1, 2, In this case two N are connected via a polyethyleneglycol linker, resulting for instance in cryptands, such as but not limited to [2.2.2]cryptand (CAS: 23978-09-8) having the formula XXXXIV below (see example 17i)

XXXXIV

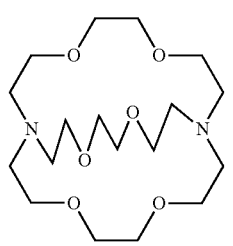

The crown or aza-crown crown ethers are all commercially available, for example by Sigma Aldrich or by VWR, or can be prepared by methods known in the art.

In a further embodiment the —CH$_2$—CH(R7)-O— units are contained in a dendrimeric compound consisting of a core and having several branches containing the —CH$_2$—CH(R7)-O— units. Such dendrimeric compounds can be based on ethylene oxide, propylene oxide or both (see block co-polymers above). In an embodiment thereof a compound of formula XXXXVI

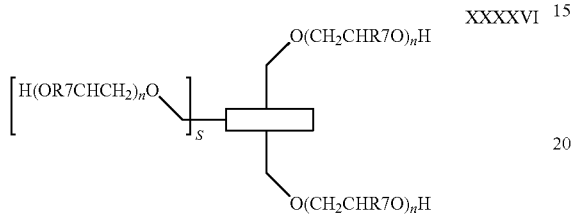

XXXXVI consisting of a core having attached O(CH$_2$—CH(R7)-O)nH units wherein s is 1 to 5 (3 to 8 branches), preferably 1 to 3 (3 to 5 branches), n is 3 to 20, starting from the core, is added to the reaction mixture. Cores which can be used are polyols such as but not limited to glycerol, trimethylolpropane, pentaerythritol or sorbitan.

Polyethylene glycol derived dendrimeric structures with R7=H which can be used for example are Glycerole ethoxylate 1000 (CAS: 31694-55-0, formula XXXXVII with R=H, m=0, n 6-7, see Example 17r herein below) or Trimethylolpropane ethoxylate (CAS: 50586-59-9, formula XXXXVII with R=Et, m=1, n=3-7)

Formula XXXXVII

H$_2$C—O(CH$_2$CH$_2$O)nH

R—|—(CH$_2$)m—O(CH$_2$CH$_2$O)nH

Hn(OCH$_2$CH$_2$)O—CH$_2$

As a further dendrimer polyoxyethylene-sorbitan monolaurate, CAS: 9005-64-5) with an average molecular weight from about 200-1000, for example Polysorbate 20 (with w+x+y+z~16, example 17s herein below) can be used as additive.

Polypropylene glycol derived dendrimeric structures with R7=CH$_3$ which can be used are for example Glycerolepropoxylate 1500 (CAS: 25791-96-2, formula XXXXIX with R=H, m=0, n~8).

XXXXIX

H$_2$C—O(CH$_2$CH(CH$_3$)O)nH

R—|—(CH$_2$)m—O(CH$_2$CH(CH$_3$)O)nH

Hn(O(CH$_3$)CHCH$_2$)O—CH$_2$

Further blockpolymers, as described above, such as but not limited to polyethoxylate-co-polypropylate can be attached to the core for example Glycerol ethoxylate-co-propoxylate triol 2600 (CAS: 51258-15-2).

Such dendrimeric compounds are commercially available for instance from Sigma Aldrich.

In a further embodiment of the process of the present invention any one of the additives of formula XXVIII, including XXXI, XXXIII, XXXVI, XXXVII, XXXVIII, and XXXIX, and XXXXII, XXXXIII, XXXXVI, is added, preferably in catalytic amounts of about 0.02 to 0.5 mass equivalents.

The product of the formula I can be isolated in a way known by a person skilled in the art. For example by removal of the solvents and the residue can be purified by column chromatography on silica.

If one component was used in excess, the compound of formula I can be isolated by aqueous work up in suitable solvent, like ethylacetate (AcOEt), tert-butylmethylether (MTBE) or toluene by washing away an excess of the base with diluted aqueous acids, for example HCl, citric acid, NaH$_2$PO$_4$ or NaHSO$_4$, drying the organic phase for example with MgSO$_4$ or Na$_2$SO$_4$, followed by azeotropic distillation and evaporation of solvents. The product of formula I can be further purified either by crystallisation, distillation or sublimation, mostly preferred is crystallisation.

In a further embodiment the present invention relates to a process for the preparation of a compound of formula II (Fexofenadine)

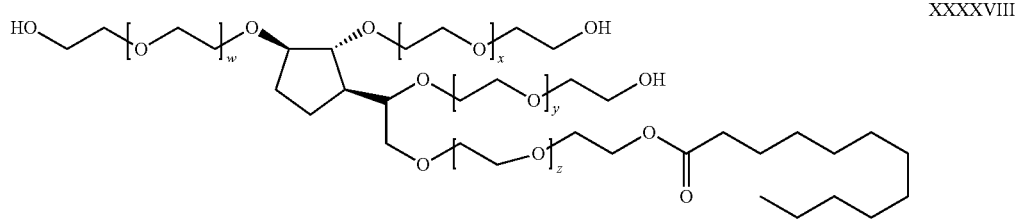

XXXXVIII

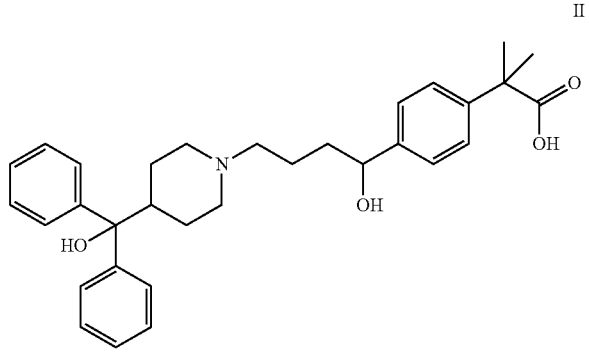 [SMILES: CC(C)(C(=O)O)c1ccc(C(O)CCCN2CCC(C(O)(c3ccccc3)c3ccccc3)CC2)cc1]

which process comprises preparing a compound of formula I according to the process as described above, and converting the compound of formula I into a compound of formula II.

The conversion of compound of formula I into a compound of formula II is known in the art such as described in published application US2003/0166682 A1 (Frederico J. Milla; Examples 9 to 11), including ring opening with halogenation, coupling with azacyclonol, reduction of the keto group and conversion of the nitril into the carboxylic acid to obtain the compound of formula II. If desired, the compound of formula II can be further converted into a pharmaceutically acceptable salt thereof, such as the HCl salt, by methods described in the art.

The invention is further described in the following examples without limiting it to them.

Abbreviations

AcOEt ethyl acetate
AUC area under curve
Bu butyl
ca. circa
d dublett
DCM dichloromethane
Et ethyl
Eq. Equivalents
h hour(s)
HPLC high performance liquid chromatography
KOtBu potassium tert.-butylate
KHMDS potassium hexamethydisilazane
LC-MS liquid chromatography-mass spectrometry
LDA Lithium diisopropylamide
LiHMDS lithium hexamethydisilazane
m multiplet
Me methyl
min minutes
MTBE methyl-tert.-butylether
NaHMDS sodium hexamethydisilazane
NMR Nuclear magnetic resonance
PEG polyethylene glycol
rt room temperature
$R_t$ retention time
s singulett
THF tetrahydrofuran
TMS tetramethylsilane

EXAMPLES

This invention is described in more detail by the examples that follow. These examples are designated to illustrate the invention, but do not limit its scope. Each step of the process described in the present invention is scalable on larger amounts than described here.

The NMR assignments are for illustration only based on analysis of the one-dimensional $^1$H NMR spectra as done by those skilled in the art. A more detailed analysis of the spectra may lead to minor reassignments of some NMR peaks, which obviously does not change the overall assignment. All $^1$H NMR spectra are recorded on a 500 MHz instrument at rt. Shifts are relative to TMS in [ppm]; the solvent is always DMSO-$d_6$.

Reference Example 1

Meta- and para-2-[(cyclopropanecarbonyl-)-phenyl]-2-methyl-propanenitrile of Formula XIX According to Scheme 6

10.1 g (75.8 mmol, 2.2 eq.) AlCl$_3$ were added to 6.4 g (45 mmol, 1.3 eq.) 4-chlorobuturylchloride at <20° C. Then 5 g (34 mmol) 2-methyl-2-phenyl-propanenitrile of formula XVIII was added. The mixture was stirred 10 h at 40-45° C. The mixture was cooled to rt poured on ice and extracted twice with DCM. The combined organic layers were washed with 1M aq. HCl and aq. sodium carbonate, dried with MgSO4 and concentrated. The intermediate compound of formula XII was taken without any purification in the next cyclisation step. The crude mixture was dissolved in 8 ml EtOH/water 1:1 and 5.5 ml aq. NaOH (32%) was added with cooling. After stirring for 2 h at rt the mixture was diluted with water and extracted twice with DCM. The combined organic layers were washed with aq. sodium bicarbonate, dried with MgSO4 and concentrated. The crude product was purified by silica chromatography with DCM/heptane 3:1 to yield 2.9 g (14 mmol, 40%) of the title compound I among with 57% of the meta-isomer XIX (separated by HPLC with a chiral stationary phase).

HPLC (DaicelCiral OD-R, 250×4.6, A. H$_2$O/0.1% HCOOH, B: MeCN/0.1% HCOOH, 10→70% B 15 min, 70%→10% 15 min, 1 ml/min, 35° C.): Meta-isomer (XIX) $R_t$=12.44 min; para-isomer (I) $R_t$=12.77 min;

NMR of the mixture (400 MHz): 1.01-1.11 (m, 8H, cyclopropyl CH$_2$), 1.73 (s, 6H, CH$_3$), 1.74 (s, 6H, CH$_3$), 2.86-2.99 (m, 2H, cyclopropyl CH), 7.63 (dd, 1H, Ar—H), 7.70 (d, 2H, Ar—H), 7.80-7.85 (m, 1H, Ar—H), 8.04-8.13 (m, 4H, Ar—H); LC-MS: MH$^+$ 214 (isomers not separated).

Reference Example 2

3-cyclopropyl-3-(4-fluorophenyl)-3-hydroxy-2,2-dimethyl-propanenitrile of Formula XXIV Using LiHMDS as Base LiHMDS (1.0M in MTBE, 7 mmol, 2.3 eq.), 1.1 ml (12 mmol, 4 eq.) isobutyronitrile and 0.5 g (3.0 mmol) cyclopropyl-(4-fluorophenyl)-methanon were allowed to stir at rt. HPLC showed complete consumption of starting material. The mixture was stirred 2 h at 50° C. without any change of the product distribution. Aqueous work up (see example 3) and crystallization from MTBE furnished 0.2 g (0.86 mmol, 29%) of the side product of formula XXIV.

HPLC: (Merck Chromolith Performance RP18e, A. H$_2$O/0.05% TFA, B: MeCN/0.05% TFA, 10→70% B 10 min, 4 ml/min, 40° C.): $R_t$=2.97 min;

NMR (600 MHz): 0.06-0.15 (m, 1H, cyclopropyl), 0.22-0.31 (m, 1H, cyclopropyl), 0.54-0.63 (m, 1H, cyclopropyl), 0.77-0.85 (m, 1H, cyclopropyl), 1.256, 1.261 (2s, 6H, CH$_3$), 1.71-1.78 (m, 1H, cyclopropyl CH), 5.00 (s, 1H, OH), 7.14-7.21 (m, 2H, Ar—H), 7.58-7.65 (m, 2H, Ar—H); LC-MS: M+ (—OH) 216.

Coupling of cyclopropyl-(4-fluorophenyl)methanon XXa with isobutyronitrile according to scheme 7

Example 3

2-[4-(cyclopropanecarbonyl-)-phenyl]-2-methyl-propanenitrile of Formula I Using KHMDS as Base Isobutyronitrile 33.7 g (487 mmol, 4 eq.) was added to 435 ml (305 mmol) 0.7M KHMDS solution in toluene at 60° C. After 10 min 20.0 g (122 mmol) cyclopropyl-(4-fluorophenyl)-methanon were slowly added at 60-62° C. The mixture was stirred 80 min at 60° C.

Aqueous work-up: The mixture was cooled to rt and poured on 500 ml aq. sodium bicarbonate. After phase separation, the organic layer was washed with aq. $Na_2CO_3$, water, $KHSO_4$, dried with $MgSO_4$ and concentrated. 25.8 g (121 mmol, 99%) of the title compound I were obtained among with 15% of the side product of formula XXV and 5% starting material according to scheme 9.

HPLC: (Merck Chromolith Performance RP18e, A. $H_2O$/0.05% TFA, B: MeCN/0.05% TFA, 10→70% B 10 min, 4 ml/min, 40° C.): Title compound I $R_t$=3.00 min; side product XXV $R_t$=3.32 min, starting material XX $R_t$=2.39 min.

From a similar reaction the side product 3-[4-(1-cyano-1-methyl-ethyl)phenyl]-3-cyclopropyl-3-hydroxy-2,2-dimethyl-propanenitrile of formula XXV was isolated as reference compound by combining silica chromatography (heptane/AcOEt) and crystallisation (MTBE).

NMR (600 MHz): 0.08-0.14 (m, 1H, cyclopropyl), 0.23-0.30 (m, 1H, cyclopropyl), 0.55-0.62 (m, 1H, cyclopropyl), 0.78-0.85 (m, 1H, cyclopropyl), 1.27 (s, 6H, $CH_3$), 1.70 (s, 6H, $CH_3$), 1.72-1.79 (m, 1H, cyclopropyl CH), 4.99 (s, 1H, OH), 7.50 (d, 2H, Ar—H), 7.64 (d, 2H, Ar—H); LC-MS: $MNa^+$ 305, $M^+$ (—OH) 265.

Example 4

2-[4-(cyclopropanecarbonyl-)-phenyl]-2-methyl-propanenitrile of Formula I Using Commercial NaHMDS as Base 5.5 ml NaHMDS (0.6M in toluene from Sigma Aldrich), 3.3 mmol, 1.1 eq.), 1.1 ml (12 mmol, 4 eq.) isobutyronitrile and 0.5 g (3.0 mmol) cyclopropyl-(4-fluorophenyl)-methanon were mixed at <35° C. for 1 h. Additional 5.5 ml of NaHMDS-solution were added and the mixture was heated to 85° C. for 3 h. Work-up (example 3) and evaporation of the solvents furnished the crude product of formula I. Analysis of the crude product revealed about 66% of the product among with 13% of starting material cyclopropyl-(4-fluorophenyl)-methanon.

Compound I: LC-MS: (YMC J' sphere ODS H 80 20×2.1 mm, 4 μm, A: $H_2O$+0.05% TFA, B: MeCN, 4%→95% B in 2 min, 1 ml/min, 30° C.): $R_t$=1.40 min-LC-MS: $MH^+$ 214; cyclopropyl-(4-fluorophenyl)methanon XXa: LC-MS: (YMC J' sphere ODS H 80 20×2.1 mm, 4 μm, A: $H_2O$+ 0.05% TFA, B: MeCN, 4%→95% B in 2 min, 1 ml/min, 30° C.): $R_t$=1.34 min.

Example 5

2-[4-(cyclopropanecarbonyl-)-phenyl]-2-methyl-propanenitrile of Formula I Using Freshly Prepared NaHMDS, from Chlorotoluene and HMDS, as Base Sodium (2.50 g, 109 mmol, 3 eq.), and 10.6 g (65.4 mmol, 1.8 eq.) HMDS in 30 ml xylene were heated to 120° C. 2-Chlorotoluene (7.6 g, 60 mmol, 1.7 eq.) was slowly added via cannula at T>130° C. The mixture was stirred 1 h at 120° C. and was cooled to 30° C. The solution so obtained was about 2M NaHMDS in xylene/toluene. To this solution isobutyronitrile (6.5 ml, 71 mmol, 2 eq.) was added, followed by cyclopropyl-(4-fluorophenyl)-methanon (5.86 g, 35.7 mmol) in 6.5 ml (2 eq.) isobutyronitrile at T<35° C. The mixture was stirred at 55° C. for 18 h and 30 min at 70° C. 30 ml water were added, the mixture was stirred for 30 min, filtered and rinsed with toluene. The organic layer was treated with aq. $NaHSO_4$ and citric acid (pH 4) and the phases were separated. The organic layer was washed with water, dried and concentrated to yield 6 g of the crude product of formula I. Analysis of the crude product revealed about 60% of the product I among with 14% of starting material and 5% of side product XXV.

The crude product was crystallized from heptane/AcOEt to yield 3.63 g (48%) of the title compound as a white solid.

NMR (600 MHz): 1.01-1.17 (m, 4H, cyclopropyl $CH_2$), 1.73 (s, 6H, $CH_3$), 2.87-2.93 (m, 1H, cyclopropyl CH), 7.70 (m, 2H, Ar—H), 8.09 (m, 2H, Ar—H).

Example 6

2-[4-(cyclopropanecarbonyl-)-phenyl]-2-methyl-propanenitrile of Formula I Using KHMDS as Base 5.0 g (25 mmol, 2.5 equ.) KHMDS powder were mixed in 25 ml toluene and the mixture was heated to 60° C. until a clear solution was obtained. 3.6 ml (40 mmol, 4 eq.) isobutyronitrile and 1.8 g (10 mmol) cyclopropyl-(4-chlorophenyl)methanon were added and the mixture was heated for 3.5 h at 60° C. Water was added in portions. Analysis of the reaction mixture by HPLC revealed about 32% of the product I and 21% of starting material.

Example 7

2-[4-(cyclopropanecarbonyl-)-phenyl]-2-methyl-propanenitrile of Formula I Using NaHMDS as Base NaHMDS, prepared from 0.76 g (33 mmol, 3 eq.) sodium in 2.32 g (18 mmol, 1.7 eq.) 2-Chlorotoluene and 3.2 g (200 mmol, 1.8 eq.) HMDS in 30 ml xylene according to example 5, was treated with 4.0 ml (44 mmol, 4 eq.) isobutyronitrile and 2.0 g (11 mmol) cyclopropyl-(4-chlorophenyl)methanon and the mixture was heated at 55-70° C. for 42 h. 10 ml of water were added, the mixture was filtered and rinsed with toluene. The organic layer washed with aq. $NaHSO_4$, dried with $Na_2SO_4$ and concentrated to yield 1.9 g of the crude product, containing about 23% of the product I and 31% of starting material XXb (HPLC).

Example 8

[4-[2-[2-[2-[2-[2-[2-[2-[2-[4-(cyclopropanecarbo-nyl)phenoxy]ethoxy]-ethoxy]ethoxy]ethoxy] ethoxy]ethoxy]ethoxy]ethoxy]phenyl]-cyclopropyl-methanone of Formula XXXIIa With n~9 (Average)

1.74 g (10.6 mmol) cyclopropyl-(4-fluorophenyl)methanon XXa, 0.53 g (14 mmol, 2.8 eq.) sodium amide, 2.0 g (4.83 mmol, 0.34 equ./PEG-400 (average n=9) were mixed in 2 ml toluene and stirred for 10 h between 30-40° C. The mixture was diluted with 5 ml toluene and treated with 40 ml water. After phase separation, the organic layer was washed with water and finally concentrated in vacuum to yield 2.98 g (4.82 mmol, 99%) of XXXIIa as a pale yellow oil in 88% purity (HPLC).

HPLC: (Merck Chromolith Performance RP18e, A. H$_2$O/ 0.05% TFA, B: MeCN/0.05% TFA, 10→70% B in 7 min, 4 ml/min, 40° C.): R$_t$=5.19 min;

NMR (400 MHz): 0.95-1.03 (m, 8H, cyclopropyl-CH$_2$), 2.79-2.90 (m, 2H, cyclopropyl CH), 3.43-3.62 (m, 26H, —OCH$_2$CH$_2$O—), 3.72-3.81 (m, 4H, —OCH$_2$CH$_2$O—), 4.15-4.25 (m, 4H, —OCH$_2$CH$_2$O—), 7.05 (d, 4H, arom.), 8.00 (d, 4H, arom.);

LC-MS: (YMC J' sphere ODS H 80 20×2.1 mm, 4 µm, A: H$_2$O+0.05% TFA, B: MeCN, 4%→95% B in 4 min, 1 ml/min, 30° C.): R$_t$=2.32 min-LC-MS: n=9: MH$^+$ 703, MNa$^+$ 725, n=8: MH$^+$ 659, MNa$^+$ 681, n=10: MH$^+$747, MNa$^+$769

Example 9

Direct Comparison of the Effect of Using a Polyether or Not Using NaHDMS as Base a) 2-[4-(cyclopropanecarbonyl-)-phenyl]-2-methyl-propanenitrile of formula I using commercial NaHMDS as base 10 ml NaHMDS (0.6M in toluene, 6 mmol, 2 eq.), 1.1 ml (12 mmol, 4 eq.) isobutyronitrile and 0.5 g (3.0 mmol) cyclopropyl-(4-fluorophenyl)-methanon were mixed at <35° C. for 1 h. The mixture was heated to 56° C. for 16 h. Water (0.1 ml) was added, the mixture was stirred for 30 min and was than cooled to rt. The mixture was treated with 30 ml Me-THF and 10 ml 2M NaSO$_4$. After phase separation, the organic layer was washed with Brine, dried with MgSO$_4$ and concentrated. Analysis of the crude product by HPLC revealed about 54% of the product among with 35% of starting material. HPLC (AUC, Merck Chromolith Performance RP18e, A. H$_2$O/0.05% TFA, B: MeCN/0.05% TFA, 10→70% B in 7 min, 4 ml/min, 40° C., UV: 210 nm): R$_t$=4.01 min; (YMC J' sphere ODS H 80 20×2.1 mm, 4 µm, A: H$_2$O+0.05% TFA, B: MeCN, 4%→95% B in 2.0 min, 1 ml/min, 30° C., UV: 220 nm; MS: ESI): R$_t$=1.43 min, MH$^+$ 214.

b) 2-[4-(cyclopropanecarbonyl-)-phenyl]-2-methyl-propanenitrile of formula I using commercial NaHMDS as base and Dimethyl-PEG 1000 of formula XXXVI with R6/R8=methyl, n~22.

10 ml NaHMDS (0.6M in toluene, 6 mmol, 2 eq.), 1.1 ml (12 mmol, 4 eq.) isobutyronitrile and 0.5 g (3.0 mmol) cyclopropyl-(4-fluorophenyl)-methanon and 100 mg (0.2 mass-eq.) Dimethyl-PEG 1000 (CAS: 24991-55-7, Sigma Aldrich) were mixed at <35° C. for 1 h. The mixture was heated to 56° C. for 16 h. Water (0.1 ml) was added, the mixture was stirred for 30 min and was than cooled to rt. The mixture was treated with 30 ml Me-THF and 10 ml 2M NaSO$_4$. After phase separation, the organic layer was washed with Brine, dried with MgSO$_4$ and concentrated. Analysis of the crude product by HPLC revealed about 74% of the product among with 5% of starting material. HPLC (AUC, Merck Chromolith Performance RP18e, A. H$_2$O/ 0.05% TFA, B: MeCN/0.05% TFA, 10→70% B in 7 min, 4 ml/min, 40° C., UV: 210 nm): R$_t$=4.00 min; (YMC J' sphere ODS H 80 20×2.1 mm, 4 µm, A: H$_2$O+0.05% TFA, B: MeCN, 4%→95% B in 2.0 min, 1 ml/min, 30° C., UV: 220 nm; MS: ESI): R$_t$=1.43 min, MH$^+$ 214.

Example 10

2-[4-(cyclopropanecarbonyl-)-phenyl]-2-methyl-propanenitrile of Formula I Using Sodium Amide as Base and PEG 1000 of Formula XXXI with n~23

16.4 g (99.9 mmol) cyclopropyl-(4-fluorophenyl)methanon of formula XX, 13.8 g (200 mmol, 2 eq.) isobutyronitrile and 4.99 g (4.99 mmol, 0.3 mass-eq.) PEG 1000 (CAS: 25322-68-3, Sigma Aldrich) were mixed in 12 ml toluene and heated to 45° C. Then 5.85 g (150 mmol, 1.5 eq.) sodium amide were added in portions over 2.5 h. After addition the mixture was stirred 4 h at 50° C. and 18 h at rt. 140 ml water were slowly added, followed by 30 ml toluene. The phases were separated and the aqueous phase was re-extracted with toluene. The combined organic layers were washed 3 times with brine, dried with MgSO$_4$ and concentrated to yield 25 g of the crude compound I. Analysis of the crude product by HPLC revealed about 77% of the product I, 3% of starting material and none of side product XXV could be detected. The crude product was crystallized from iPrOH/water to yield 13.4 g (63%) of the title compound as a white solid. mp: 85° C. (iPrOH/water).

Further Examples showing the use of different kinds of polyethers

Example 11

2-[4-(cyclopropanecarbonyl-)-phenyl]-2-methyl-propanenitrile of Formula I Using Sodium Amide as Base and PEG 1000 of Formula XXXI with n~20

4.95 g (27.4 mmol) cyclopropyl-(4-chlorophenyl)methanon, 3.79 g (54.8 mmol, 2 eq.) isobutyronitrile and 0.69 g (0.69 mmol, 0.14 mass. eq.) PEG 1000 (Sigma Aldrich) were mixed in 3.2 ml toluene and heated to 50° C. Then 1.60 g (41.1 mmol, 1.5 eq.) sodium amide were added in portions. After addition the mixture was stirred 5 h at 55° C. Analysis of the reaction mixture by HPLC (see example 9) revealed about 27% of the product I and 31% of starting material.

Example 12

2-[4-(cyclopropanecarbonyl-)-phenyl]-2-methyl-propanenitrile of Formula I Using Sodium Amide as Base and PEG 1500 of Formula XXXI With n~34

18.9 g (110 mmol) cyclopropyl-(4-fluorophenyl)methanon (95% purity), 40 ml (0.45 mol, 4 eq.) isobutyronitrile and 2.75 g (0.15 mass-eq.) PEG 1500 (CAS: 25322-68-3, Merck) and sodium amide (6.42 g, 165 mmol, 1.5 eq.) were allowed to react in 7.2 ml toluene as described in example 10 to yield 16.7 g (72%) of the title compound I in 99.5% purity (HPLC) after crystallization. HPLC (AUC, Merck Chromolith Performance RP18e, A. H$_2$O/0.05% TFA, B: MeCN/0.05% TFA, 10→70% B in 7 min, 4 ml/min, 40° C., UV: 210 nm): R$_t$=4.01 min; (YMC J' sphere ODS H 80 20×2.1 mm, 4 µm, A: H$_2$O+0.05% TFA, B: MeCN, 4%→95% B in 3.8 min, 1 ml/min, 30° C., UV: 220 nm; MS: ESI): R$_t$=2.08 min, MH$^+$ 214.

Example 13

2-[4-(cyclopropanecarbonyl-)-phenyl]-2-methyl-propanenitrile of Formula I Using Sodium Amide as Base and PEG 2000 of Formula XXXI With n~45

18.0 g (110 mmol) cyclopropyl-(4-fluorophenyl)methanon, 40 ml (0.45 mol, 4 eq.) isobutyronitrile and 2.75 g (0.15 mass-eq.) PEG 2000 (CAS: 25322-68-3, Sigma Aldrich) and sodium amide (6.42 g, 165 mmol, 1.5 eq.) were allowed to react in 5.4 ml toluene and finally worked-up as described in example 10 to yield 18.4 g (79%) of the title compound I in 99.8% purity (HPLC) after crystallization from iPrOH/water. HPLC (AUC, Merck Chromolith Performance RP18e, A. $H_2O$/0.05% TFA, B: MeCN/0.05% TFA, 10→70% B in 7 min, 4 ml/min, 40° C., UV: 210 nm): $R_t$=4.03 min; (YMC J' sphere ODS H 80 20×2.1 mm, 4 µm, A: $H_2O$+0.05% TFA, B: MeCN, 4%→95% B in 3.8 min, 1 ml/min, 30° C., UV: 220 nm; MS: ESI): $R_t$=2.10 min, $MH^+$214.

Example 14

2-[4-(cyclopropanecarbonyl-)-phenyl]-2-methyl-propanenitrile of Formula I Using Sodium Amide as Base and PEG 3500 of Formula XXXI with n~80

18.9 g (110 mmol) cyclopropyl-(4-fluorophenyl)methanon (95% purity), 40 ml (0.45 mol, 4 eq.) isobutyronitrile and 2.75 g (0.15 mass-eq.) PEG 3500 (CAS: 25322-68-3, Sigma Aldrich) and sodium amide (6.42 g, 165 mmol, 1.5 eq.) were allowed to react in 7.2 ml toluene and finally worked-up as described in example 10 to yield 17.9 g (77%) of the title compound I in 99.7% purity (HPLC) after crystallization from iPrOH/water. HPLC (AUC, Merck Chromolith Performance RP18e, A. $H_2O$/0.05% TFA, B: MeCN/0.05% TFA, 10→70% B in 7 min, 4 ml/min, 40° C., UV: 210 nm): $R_t$=4.01 min; (YMC J' sphere ODS H 80 20×2.1 mm, 4 µm, A: $H_2O$+0.05% TFA, B: MeCN, 4%→95% B in 3.8 min, 1 ml/min, 30° C., UV: 220 nm; MS: ESI): $R_t$=2.08 min, $MH^+$ 214.

Example 15

2-[4-(cyclopropanecarbonyl-)-phenyl]-2-methyl-propanenitrile of Formula I Using Sodium Amide as Base and Dimethyl-PEG 500 of Formula XXXVI with R6/R8=methyl, n~11

18.0 g (110 mmol) cyclopropyl-(4-fluorophenyl)methanon, 40 ml (0.45 mol, 4 eq.) isobutyronitrile and 2.75 g (0.15 mass-eq.) Dimethyl-PEG500 (CAS: 24991-55-7, Sigma Aldrich) were mixed in 5.4 ml toluene. Sodium amide (6.42 g, 165 mmol, 1.5 eq.) was added at rt. After addition the mixture was stirred 1 h at rt, 2 h at 30° C. and 18 h at 40° C. Water (0.4 ml) was added, the mixture was stirred for 30 min and was then added to 170 ml water. The phases were separated, the organic layer was washed with 40 ml water and concentrated. The residue was crystallized form iPrOH/water to yield 19.0 g (81%) of the title compound I in 99.8% purity (HPLC). HPLC (AUC, Merck Chromolith Performance RP18e, A. $H_2O$/0.05% TFA, B: MeCN/0.05% TFA, 10→70% B in 7 min, 4 ml/min, 40° C., UV: 210 nm): $R_t$=4.03 min; (YMC J' sphere ODS H 80 20×2.1 mm, 4 µm, A: $H_2O$+0.05% TFA, B: MeCN, 4%→95% B in 3.8 min, 1 ml/min, 30° C., UV: 220 nm; MS: ESI): $R_t$=1.99 min, $MH^+$ 214; NMR (400 MHz): 1.00-1.09 (m, 4H, cyclopropyl $CH_2$), 1.72 (s, 6H, $CH_3$), 2.86-2.94 (m, 1H, cyclopropyl CH), 7.69 (m, 2H, Ar—H), 8.09 (m, 2H, Ar—H); mp: 86-87° C. (iPrOH/water).

Example 16

2-[4-(cyclopropanecarbonyl-)-phenyl]-2-methyl-propanenitrile of Formula I Using Sodium Amide as Base and Dimethyl-PEG 2000 of Formula XXXVI With R6/R8=methyl, n~44

18.8 g (110 mmol) cyclopropyl-(4-fluorophenyl)methanon (95% purity), 4 ml (0.45 mol, 4 eq.) isobutyronitrile and 2.70 g (0.15 mass-eq.) Dimethyl-PEG2000 (CAS: 24991-55-7, Merck) were mixed in 7.1 ml toluene. Sodium amide (6.4 g, 0.16 mol, 1.5 eq.) was added at rt. After addition the mixture was stirred 1 h at rt, 2 h at 30° C. and 17 h at 40° C. Water (0.4 ml) was added, the mixture was stirred for 40 min at 40° C. and was than added to 120 ml water and 10 ml toluene. The phases were separated, the organic layer was washed with 40 ml water and concentrated. The residue was crystallized form iPrOH/water to yield 17.5 g (75%) of the title compound I in 99.7% purity (HPLC). HPLC (AUC, Merck Chromolith Performance RP18e, A. $H_2O$/0.05% TFA, B: MeCN/0.05% TFA, 10→70% B in 7 min, 4 ml/min, 40° C., UV: 210 nm): $R_t$=4.03 min; (YMC J' sphere ODS H 80 20×2.1 mm, 4 µm, A: $H_2O$+0.05% TFA, B: MeCN, 4%→95% B in 3.8 min, 1 ml/min, 30° C., UV: 220 nm; MS: ESI): $R_t$=2.10 min, $MH^+$ 214.

Example 17

Further activator/polyether evaluation based on a general procedure for preparing 2-[4-(cyclopropanecarbonyl-)-phenyl]-2-methyl-propanenitrile of formula I using sodium amide as base and different polyoxyalkylene additives:

Sodium amide (1.6 g, 41 mmol, 1.5 eq.) was placed in a 100 ml three-necked round bottom flask. Toluene (3.8 ml) and isobutyronitrile (5.0 ml, 54 mmol, 2 eq.) were added, followed by 0.68 g (0.15 mass-equivalents or 15 wt.-%) of PEG or PPG. Then cyclopropyl-(4-fluorophenyl)methanon (4.5 g, 27 mmol, 1.0 eq.) was added at rt. The mixture was stirred 1 h at rt, 2 h at 30° C. and at 40° C. over night. The mixture was cooled to rt, water (0.1 ml) was added and stirring was continued for 30 min. The mixture was added to 40 ml water, rinsed with 4 ml toluene and stirred at 45° C. for 30 min. After phase separation the organic layer was extracted with 10 ml water at 45° C. After phase separation the organic layer was removed in vacuum. iPrOH (10 ml) was added and removed by distillation. The crude product of formula I so obtained was analysed by HPLC (AUC, Merck Chromolith Performance RP18e, A. $H_2O$/0.05% TFA, B: MeCN/0.05% TFA, 10→70% B in 7 min, 4 ml/min, 40° C., UV: 210 nm) and LC-MS-Method short gradient (YMC J' sphere ODS H 80 20×2.1 mm, 4 µm, A: $H_2O$+0.05% TFA, B: MeCN, 4%→95% B in 2 min, 1 ml/min, 30° C.; UV: 220 nm; MS: ESI), Method long gradient: (YMC J' sphere ODS H 80 20×2.1 mm, 4 µm, A: $H_2O$+0.05% TFA, B: MeCN, 4%→95% B in 3.8 min, 1 ml/min, 30° C., UV: 220 nm; MS: ESI).

Example a

Reaction was performed as described in the general procedure without any additive to yield the title compound. HPLC: 46% yield (AUC), $R_t$=4.04 min; LC-MS (long): $R_t$=1.98 min, MH$^+$214.

Example b

Dimethyl-PEG 500 of formula XXVIII with R7=H, R6, R8=methyl, n~11 (CAS: 24991-55-7) from Merck was used as described in the general procedure to yield the title compound. HPLC: 86% yield (AUC), $R_t$=4.11 min; LC-MS (short): $R_t$=1.36 min, MH$^+$ 214.

Example c

Dimethyl-PEG 1000 of formula XXVIII with R7=H, R6, R8=methyl, n~22 (CAS: 24991-55-7) from Sigma Aldrich was used as described in the general procedure to yield the title compound. HPLC: 85% yield (AUC), $R_t$=4.11 min; LC-MS (short): $R_t$=1.36 min, MH$^+$ 214.

Example d

Triethylene glycol dimethyl ether of formula XXVIII with R7=H, R6, R8=methyl, n=3 (CAS: 112-49-2) from Acros was used as described in the general procedure to yield the title compound. HPLC: 60% yield (AUC), $R_t$=4.05 min; LC-MS (long): $R_t$=1.98 min, MH$^+$ 214.

Example e

12-Crown-4 of formula XXXXII with n=4 (CAS: 294-93-9) from Sigma Aldrich was used as described in the general procedure to yield the title compound. HPLC: 88% yield (AUC), $R_t$=4.05 min; LC-MS (long): $R_t$=1.98 min, MH$^+$ 214.

Example f

15-Crown-5 of formula XXXXII with n=5 (CAS: 33100-27-5) from Sigma Aldrich was used as described in the general procedure to yield the title compound. HPLC: 82% yield (AUC), $R_t$=4.10 min; LC-MS (long): $R_t$=1.96 min, MH$^+$ 214.

Example g

Dicyclohexyl 18-Crown-6 of formula XXXXII with n=6 (CAS: 16069-36-3) from Sigma Aldrich was used as described in the general procedure to yield the title compound. HPLC: 87% yield (AUC), $R_t$=4.09 min; LC-MS (short): $R_t$=1.37 min, MH$^+$ 214.

Example h

N,N'-Dibenzyl-4,13-diaza-18-crown 6-Ether of formula XXXXIII (m, n=1, Rx, Ry=benzyl, CAS: 69703-25-9) from Sigma Aldrich was used as described in the general procedure to yield the title compound. HPLC: 84% yield (AUC), $R_t$=4.04 min; LC-MS (long): Rt=1.98 min, MH+ 214.

Example i 4,7,13,16,21,24-Hexaoxa-1,10-diazabicyclo[8.8.8]hexacosan—Kryptofix® 222 of formula XXXXIV (CAS: 23978-09-8) from Sigma Aldrich was used as described in the general procedure to yield the title compound. HPLC: 82% yield (AUC), $R_t$=4.04 min; LC-MS (long): Rt=1.98 min, MH+ 214.

Example j

Monobutyl-PPG 2500 of formula XXXVIII (with R6=butyl and n~40, CAS: 9003-13-8) from Sigma Aldrich was used as described in the general procedure to yield the title compound. HPLC: 62% yield (AUC), $R_t$=4.05 min; LC-MS (long): $R_t$=1.98 min, MH$^+$ 214.

Example k

PPG 4000 of formula XXXVII with n~70 (CAS: 25322-69-4) from ABCR was used as described in the general procedure to yield the title compound. HPLC: 59% yield (AUC), $R_t$=4.10 min; LC-MS (long): $R_t$=1.96 min, MH$^+$ 214.

Example l

PEG 20000 of formula XXXI with n~450 (CAS: 25322-68-3) from Merck was used as described in the general procedure to yield the title compound. HPLC: 86% yield (AUC), $R_t$=4.11 min; LC-MS (long): $R_t$=1.96 min, MH$^+$ 214.

Example m

PEG 1 000 000 of formula XXXI with n~23 000 (CAS: 25322-68-3) from Sigma Aldrich was used as described in the general procedure to yield the title compound. HPLC: 73% yield (AUC), $R_t$=4.07 min; LC-MS (long): $R_t$=1.98 min, MH$^+$ 214.

Example n

PEG 8 000 000 of formula XXXI with n~200 000 (CAS: 25322-68-3) from Sigma Aldrich was used as described in the general procedure to yield the title compound. HPLC: 74% yield (AUC), $R_t$=4.08 min; LC-MS (long): $R_t$=1.98 min, MH$^+$ 214.

Example o

PEG-PPG-PEG 1900 (Pluronic® 35) of formula XXXVIa (CAS: 9003-11-6) from Sigma Aldrich was used as described in the general procedure to yield the title compound. HPLC: 71% yield (AUC), $R_t$=4.04 min; LC-MS (long): $R_t$=1.98 min, MH$^+$214.

Example p

O,O-Bis-2-aminopropyl-PPG-PEG-PPG 1900 (Jeffamine®) of formula XXXVIb (with R6,R8=2-aminopropyl, x~9, y+z~3.6), (CAS: 65605-36-9) from Sigma Aldrich was used as described in the general procedure to yield the title compound. HPLC: 79% yield (AUC), $R_t$=4.04 min; LC-MS (long): $R_t$=1.98 min, MH$^+$ 214.

Example q

Octadec-9-enyl-PEG 1150 (Brij® O20) of formula XXXIII (with R7=H, R6=C18H35, R=H, n~20, CAS: 9004-98-2) from Sigma Aldrich was used as described in the general procedure to yield the title compound. HPLC: 81% yield (AUC), $R_t$=4.06 min; LC-MS (long): $R_t$=1.98 min, MH+ 214.

Example r

Glycerol-PEG 1000 of formula XXXXVII with R=H with n~7 (CAS: 31694-55-0) from Sigma Aldrich was used as described in the general procedure to yield the title compound. HPLC: 75% yield (AUC), $R_t$=4.04 min; LC-MS (long): $R_t$=1.99 min, MH+ 214.

Example s

PEG-sorbitan-monolaurate (Tween® 20) of formula XXXXVIII (CAS: 9005-64-4) from Sigma Aldrich was used as described in the general procedure to yield the title compound. HPLC: 66% yield (AUC), $R_t$=4.04 min; LC-MS (long): $R_t$=1.98 min, MH+ 214.

Example 18

2-[4-(cyclopropanecarbonyl-)-phenyl]-2-methyl-propanenitrile of Formula I Using Sodium Amide and No Additional Solvents 328 mg (2 mmol) cyclopropyl-(4-fluorophenyl)methanon, 0.5 ml (0.54 mmol, 2.7 eq.) isobutyronitrile and sodium amide (156 mg, 4 mmol, 2 eq.) were heated to 60° C. for 30 min. Analysis of the crude product by HPLC revealed about 39% of the product among with 22% of starting material.

HPLC (AUC, Merck Chromolith Performance RP18e, A. H$_2$O/0.05% TFA, B: MeCN/0.05% TFA, 10→70% B in 7 min, 4 ml/min, 40° C., UV: 210 nm): $R_t$=2.97 min (YMC J' sphere ODS H 80 20×2.1 mm, 4 μm, A: H$_2$O+0.05% TFA, B: MeCN, 4%→95% B in 2.0 min, 1 ml/min, 30° C., UV: 220 nm; MS: ESI): $R_t$=1.39 min, MH+ 214.)

The invention claimed is:

1. A process for preparing a compound of formula I

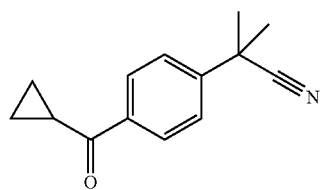

comprising reacting a compound of formula XX

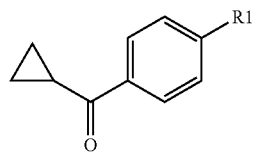

wherein R1 is fluoro or chloro,
with isobutyronitrile of formula XXI

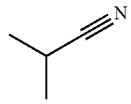

in the presence of a base, wherein the base is potassium hexamethyldisilazane (KHMDS), sodium hexamethyldisilazane (NaHMDS) or sodium amide.

2. The process according to claim 1, wherein the process is carried out in the presence of a polyethylene glycol (PEG) or polypropylene glycol (PPG) of formula HO(CH$_2$—CH(R7)-O)$_n$H, or a mixture thereof, which is unsubstituted or substituted at one or both ends, and wherein each R7 is independently H or CH$_3$, and n is from 3 to 200,000.

3. The process according to claim 1, wherein the process is carried out in the presence of a compound of formula XXVIII R6O(CH$_2$—CH(R7)-O)$_n$R8   XXVIII wherein:
n is 3-200,000;
R6 and R8 are independently H, (C1-C18)alkyl, (C3-C18) alkenyl, phenyl, —CH$_2$-phenyl, 2-aminopropyl, 3-sulfopropyl, glycidyl or C(=O)R9;
each R7 is independently H or CH$_3$; and
R9 is (C1-C17)alkyl, (C2-C17) alkenyl, or phenyl,
wherein each phenyl is independently unsubstituted or substituted by one or two groups independently selected from the group consisting of (C1-C12)alkyl and halogen.

4. The process according to claim 3, wherein each R7 is H.

5. The process according to claim 3, wherein each R7 is CH$_3$.

6. The process according to claim 3, wherein R6 and R8 are independently H, (C1-C18)alkyl, (C3-C18)alkenyl or 2-aminopropyl.

7. The process according to claim 3, wherein R6 and R8 are independently H or (C1-C18)alkyl.

8. The process according to claim 3, wherein R6 and R8 are independently (C1-C18)alkyl.

9. The process according to claim 3, wherein R6 and R8 are each H.

10. The process according to claim 3, wherein R9 is (C1-C17)alkyl, vinyl, 2-propenyl, heptadec-8-enyl or phenyl.

11. The process according to claim 1, wherein the process is carried out in the presence of a cyclic polyethylene glycol (CPG) of formula XXXXII (—CH$_2$CH$_2$O—)$_n$   XXXXII wherein n is 4-8; and
wherein one or more —CH$_2$—CH$_2$— groups is optionally replaced by phenyl or cyclohexyl.

12. The process according to claim 1, wherein the process is carried out in the presence of a compound of formula XXXXIII

XXXXIII wherein:
n is 0, 1, or 2;
m is 0, 1, or 2; and
Rx and Ry are independently H, (C1-C8)alkyl or benzyl, or
Rx and Ry are taken together to form —(CH$_2$CH$_2$—O)$_z$—CH$_2$CH$_2$—, wherein z is 1 or 2.

13. The process according to claim 1, wherein the process is carried out in the presence of a dendrimeric compound consisting of a core and 3-8 branches containing —O—(CH$_2$—CH(R7)-O)$_n$H units, which are unsubstituted or substituted at one end, and wherein each R7 is independently H or CH$_3$, and n is 3 to 20.

14. The process according to claim 2, wherein the PEG, PPG, or mixture thereof is added in the range of 0.02 to 0.50 mass equivalents relative to the compound of formula XX.

15. A process for preparing a compound of formula II

II or a pharmaceutically acceptable salt thereof comprising:
(a) preparing the compound of formula I according to claim 1;
(b) reacting the compound of formula I by ring opening with halogenation, coupling with azacyclonol, reducing a keto group, and converting a nitrile into a carboxylic acid to form the compound of formula II; and
(c) optionally converting the compound of formula II into a pharmaceutically acceptable salt thereof.

16. The process of claim 3, wherein n is 5-5,000.

17. The process of claim 3, wherein:
R6 and R8 are independently H or CH$_3$; and
each R7 is independently H or CH$_3$.

18. The process of claim 3, wherein:
n is 20-90;
R6 and R8 are each H; and
each R7 is H.

19. The process of claim 3, wherein:
n is 11-44;
R6 and R8 are each CH$_3$; and
each R7 is H.

20. The process of claim 3, wherein:
n is 4-140;
$R^6$ and $R^8$ are each H; and
each R7 is CH$_3$.

21. The process according to claim 3, wherein the compound of formula XXVIII is added in the range of 0.02 to 0.50 mass equivalents relative to the compound of formula XX.

22. The process according to claim 11, wherein the compound of formula XXXXII is added in the range of 0.02 to 0.50 mass equivalents relative to the compound of formula XX.

23. The process according to claim 12, wherein the compound of formula XXXXIII is added in the range of 0.02 to 0.50 mass equivalents relative to the compound of formula II.

24. The process according to claim 13, wherein the dendrimeric compound is added in the range of 0.02 to 0.50 mass equivalents relative to the compound of formula II.

* * * * *

UNITED STATES PATENT AND TRADEMARK OFFICE
CERTIFICATE OF CORRECTION

PATENT NO. : 10,336,698 B2  
APPLICATION NO. : 15/544493  
DATED : July 2, 2019  
INVENTOR(S) : Hermut Wehlan et al.

It is certified that error appears in the above-identified patent and that said Letters Patent is hereby corrected as shown below:

On the Title Page

In Item (56), "References Cited", right column under "OTHER PUBLICATIONS", before Caubere: please add the following four publications:
-- BRANNOCK, M.C. et al. (December 31, 2011). "Overcoming Challenges in the Palladium-catalyzed Synthesis of Electron Deficient *Ortho*-substituted Aryl Acetonitriles," *Organic & Biomolecular Chemistry* 9:2661-2666.
BRANNOCK, G. et al. (2011). "Overcoming Challenges in the Palladium-Catalyzed Synthesis of Electron Deficient Ortho-Substituted Aryl Acetonitriles," *Org. Biomol. Chem.* 9:2661-2666, Supplementary Information.
CARON, S. et al. (2000; e-published on January 12, 2000). "Preparation of Tertiary Benzylic Nitriles from Aryl Fluorides," *J. Am. Chem. Soc.* 122(4):712-713.
CARRE, M.C. et al. (1989). "Arynic Condensation of Nitrile Anions in the Presence of the Complex Base NaNH$_2$-CH$_3$CH$_2$(OCH$_2$CH$_2$)$_2$Ona," *Synthetic Communication* 19(19):3323-3330. --.

Signed and Sealed this  
Fifth Day of November, 2019

Andrei Iancu  
*Director of the United States Patent and Trademark Office*